(12) United States Patent
Urich

(10) Patent No.: US 12,133,816 B2
(45) Date of Patent: *Nov. 5, 2024

(54) PHACOEMULSIFICATION CIRCUIT

(71) Applicant: Johnson & Johnson Surgical Vision, Inc., Irvine, CA (US)

(72) Inventor: Alex Urich, Coto de Caza, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 895 days.

This patent is subject to a terminal disclaimer.

(21) Appl. No.: 17/203,637

(22) Filed: Mar. 16, 2021

(65) Prior Publication Data
US 2021/0196515 A1 Jul. 1, 2021

Related U.S. Application Data

(63) Continuation-in-part of application No. 17/094,426, filed on Nov. 10, 2020, now Pat. No. 11,191,669, which is a continuation of application No. 16/821,051, filed on Mar. 17, 2020, now Pat. No. 11,197,778, which is a continuation-in-part of application No. 14/517,798, filed on Oct. 17, 2014, now Pat. No. 10,596,033, which is a
(Continued)

(51) Int. Cl.
*A61F 9/007* (2006.01)
*A61M 1/00* (2006.01)

(52) U.S. Cl.
CPC ......... *A61F 9/00745* (2013.01); *A61M 1/774* (2021.05); *A61M 1/84* (2021.05); *A61M 2210/0612* (2013.01)

(58) Field of Classification Search
CPC ..... A61F 9/00745; A61M 1/774; A61M 1/84; A61M 2210/0612
See application file for complete search history.

(56) References Cited

U.S. PATENT DOCUMENTS

| | | |
|---|---|---|
| 3,857,387 A | 12/1974 | Shock |
| 3,941,122 A | 3/1976 | Jones |
| 3,990,452 A | 11/1976 | Murry et al. |

(Continued)

FOREIGN PATENT DOCUMENTS

| | | |
|---|---|---|
| CN | 104055621 B | 3/2017 |
| EP | 1212021 B1 | 9/2006 |

(Continued)

*Primary Examiner* — Phong Son H Dang

(57) ABSTRACT

Disclosed is a surgical instrument directed to phacoemulsification for cataract eye surgery. The instrument generally includes a dual frequency voltage producing circuit comprising a low-frequency voltage pathway with a low-frequency LC Network and a high-frequency voltage pathway with a high-frequency LC network. A phacoemulsification needle extends from a handpiece able to be driven by a piezoelectric transducer. The piezoelectric transducer is electrically connected to the dual frequency voltage producing circuit. The high-frequency voltage pathway is electrically tuned with the physical high natural frequency of the handpiece and the low-frequency voltage pathway is electrically tuned with the physical low natural frequency of the handpiece for efficient transfer of energy.

20 Claims, 21 Drawing Sheets

Related U.S. Application Data continuation-in-part of application No. 13/430,633, filed on Mar. 26, 2012, now Pat. No. 9,216,035.

(60) Provisional application No. 62/991,434, filed on Mar. 18, 2020.

(56) References Cited

U.S. PATENT DOCUMENTS

| | | |
|---|---|---|
| 4,428,748 A | 1/1984 | Peyman et al. |
| 4,864,547 A | 9/1989 | Krsna |
| 4,868,445 A | 9/1989 | Wand |
| 4,989,588 A | 2/1991 | Kubota et al. |
| 5,001,649 A | 3/1991 | Lo et al. |
| 5,062,827 A | 11/1991 | Wiksell |
| 5,112,300 A | 5/1992 | Ureche |
| 5,123,903 A | 6/1992 | Quaid et al. |
| 5,171,387 A | 12/1992 | Wuchinich |
| 5,176,677 A | 1/1993 | Wuchinich |
| 5,180,363 A | 1/1993 | Idemoto et al. |
| 5,213,569 A | 5/1993 | Davis |
| 5,255,669 A | 10/1993 | Kubota et al. |
| 5,261,922 A | 11/1993 | Hood |
| 5,269,297 A | 12/1993 | Weng et al. |
| 5,276,376 A | 1/1994 | Puskas |
| 5,346,469 A | 9/1994 | Ikeda et al. |
| 5,387,180 A | 2/1995 | Lehmer |
| 5,388,569 A | 2/1995 | Kepley |
| 5,391,144 A | 2/1995 | Sakurai et al. |
| 5,431,664 A | 7/1995 | Ureche et al. |
| 5,630,420 A | 5/1997 | Vaitekunas |
| 5,695,510 A | 12/1997 | Hood |
| 5,897,569 A | 4/1999 | Kellogg et al. |
| 5,938,677 A | 8/1999 | Boukhny et al. |
| 6,319,220 B1 | 11/2001 | Bylsma |
| 6,433,464 B2 | 8/2002 | Jones |
| 6,733,451 B2 | 5/2004 | Rabiner et al. |
| 6,884,252 B1 | 4/2005 | Urich et al. |
| 6,955,680 B2 | 10/2005 | Satou et al. |
| 6,984,220 B2 | 1/2006 | Wuchinich |
| 7,083,589 B2 | 8/2006 | Banko et al. |
| 7,273,483 B2 | 9/2007 | Wiener et al. |
| 7,431,728 B2 | 10/2008 | Gerry et al. |
| 7,794,414 B2 | 9/2010 | Rabiner et al. |
| 7,876,025 B2 | 1/2011 | Ma et al. |
| 8,009,508 B2 | 8/2011 | Young et al. |
| 8,277,462 B2 | 10/2012 | Heymann et al. |
| 8,303,530 B2 | 11/2012 | Injev et al. |
| 8,303,613 B2 | 11/2012 | Crandall et al. |
| 8,439,938 B2 | 5/2013 | Moore, Jr. |
| 8,512,325 B2 | 8/2013 | Mathonnet |
| 8,652,073 B2 | 2/2014 | Romano et al. |
| 9,060,776 B2 | 6/2015 | Yates et al. |
| 9,173,672 B2 | 11/2015 | Young et al. |
| 9,283,113 B2 | 3/2016 | Chon et al. |
| 9,339,284 B2 | 5/2016 | Du et al. |
| 9,504,471 B2 | 11/2016 | Vaitekunas et al. |
| 9,572,711 B2 | 2/2017 | Raney et al. |
| 9,622,749 B2 | 4/2017 | Vaitekunas et al. |
| 9,623,237 B2 | 4/2017 | Turner et al. |
| 9,693,897 B2 | 7/2017 | Vezzu |
| 10,052,120 B2 | 8/2018 | Du et al. |
| 10,194,972 B2 | 2/2019 | Yates et al. |
| 10,194,973 B2 | 2/2019 | Wiener et al. |
| 10,263,171 B2 | 4/2019 | Wiener et al. |
| 10,265,117 B2 | 4/2019 | Wiener et al. |
| 10,278,861 B2 | 5/2019 | Bourne |
| 10,470,788 B2 | 11/2019 | Sinelnikov |
| 10,631,909 B2 | 4/2020 | Eichler |
| 2002/0099400 A1 | 7/2002 | Wolf et al. |
| 2005/0096680 A1* | 5/2005 | Zacharias ............ A61F 9/00745 606/107 |
| 2005/0187514 A1 | 8/2005 | Rabiner et al. |
| 2005/0234473 A1 | 10/2005 | Zacharias |
| 2006/0235306 A1 | 10/2006 | Cotter et al. |
| 2007/0060926 A1* | 3/2007 | Escaf ................. A61F 9/00745 606/107 |
| 2007/0249941 A1 | 10/2007 | Salehi et al. |
| 2007/0249942 A1 | 10/2007 | Salehi et al. |
| 2008/0294087 A1 | 11/2008 | Steen et al. |
| 2009/0069712 A1 | 3/2009 | Mulvihill et al. |
| 2009/0143796 A1 | 6/2009 | Stulen et al. |
| 2010/0069825 A1 | 3/2010 | Raney |
| 2011/0166502 A1* | 7/2011 | Nallakrishnan ..... A61F 9/00736 604/22 |
| 2012/0302941 A1 | 11/2012 | Teodorescu et al. |
| 2013/0237993 A1* | 9/2013 | Nallakrishnan ..... A61F 9/00745 606/107 |
| 2015/0045806 A1 | 2/2015 | Urich et al. |
| 2016/0175150 A1 | 6/2016 | Banko |
| 2017/0087014 A1 | 3/2017 | Potter, Jr. et al. |
| 2019/0133822 A1 | 5/2019 | Banko |
| 2019/0336161 A1 | 11/2019 | Scheller et al. |
| 2020/0107848 A1 | 4/2020 | Apperson et al. |

FOREIGN PATENT DOCUMENTS

| | | |
|---|---|---|
| EP | 1215881 B1 | 4/2009 |
| EP | 2760399 B1 | 12/2016 |
| WO | 0124716 A1 | 4/2001 |

* cited by examiner

PHACOEMULSIFICATION CIRCUIT

CROSS-REFERENCE TO RELATED APPLICATIONS

This application is a Continuation-In-Part application claiming the priority to and the benefit of both U.S. Provisional Patent Application No. 62/991,434 entitled DUAL FREQUENCY ULTRASONIC PHACO SYSTEM FOR CATARACT SURGERY filed on Mar. 18, 2020 and U.S. patent application Ser. No. 17/094,426 entitled TAPERED STRUCTURE IN A PHACOEMULSIFICATION DEVICE FOR NODE PLACEMENT filed on Nov. 10, 2020, which is a Continuation application claiming the priority to and the benefit of U.S. patent application Ser. No. 16/821,051 entitled TAPERED STRUCTURE IN A PHACOEMULSIFICATION DEVICE FOR NODE PLACEMENT filed on Mar. 17, 2020, which is a Continuation-In-Part application claiming the priority to and the benefit of U.S. patent application Ser. No. 14/517,798, now U.S. Pat. No. 10,596,033, entitle PHACOEMULSIFICATION ULTRASONIC DEVICE SWITCHING BETWEEN DIFFERENT OPERATIONAL MODES, filed on Oct. 17, 2014, which is a Continuation-In-Part application claiming the priority to and the benefit of U.S. patent application Ser. No. 13/430,633, now U.S. Pat. No. 9,216,035 entitled SURGICAL INSTRUMENT RINGING A TITANIUM NEEDLE WITH A NODE OF MINIMUM AMPLITUDE IN A SUBSTANTIALLY CYLINDRICAL PORTION OF THE NEEDLE, filed on Mar. 26, 2012.

FIELD OF THE INVENTION

The present invention relates generally to the field of medical devices used in eye surgery, and more particularly to tools and methods applied to phacoemulsification procedures.

BACKGROUND

Needles that are actuated at ultrasonic frequencies may be used in various contemporary eye surgical procedures. For example, the lens of a human eye may develop a cataractous condition that affects a patient's vision. Cataractous lenses are sometimes removed and replaced in a procedure commonly referred to as phacoemulsification. Phacoemulsification procedures are typically performed with a handpiece that actuates a needle at ultrasonic frequencies. The needle is inserted through an incision in the cornea up to a desired insertion depth, and then ultrasonic actuation at one specific frequency is used to break the lens within the lens capsule of the eye. The broken lens may be removed through an aspiration line that is coupled to the handpiece, drawing irrigation fluid and aspirated tissue from a hollow passage through the needle. It is to improvements in ultrasonic actuation of a phacoemulsification needle that embodiments of the present invention are generally directed.

SUMMARY

The present invention is directed to embodiments of a phacoemulsification device and circuitry that can switch between equal to or above 60 kHz and below 60 kHz. The two frequencies produce different surgical effects when used to emulsify a cataractous lens.

Certain embodiments of the present invention can therefore comprise a phacoemulsification arrangement having a hollow needle extending from a handpiece that includes a piezoelectric crystal transducer connected to a dual frequency producing circuit comprising a low-frequency oscillator and a high-frequency oscillator. The dual frequency producing circuit electrically connected to the piezoelectric crystal transducer by way of wires. The low-frequency oscillator is configured to drive the piezoelectric crystal transducer to periodically vibrate the hollow needle at a low frequency defined as being less than 60 kHz without producing a node of minimum amplitude along the hollow needle. The high-frequency oscillator is configured to drive the piezoelectric crystal transducer to periodically vibrate the hollow needle at a high frequency of more than or equal to 60 kHz while producing a single node of minimum amplitude along the hollow needle. The high-frequency voltage pathway is electrically tuned with the physical high natural frequency of the handpiece (and possibly the needle) and the low-frequency voltage pathway is electrically tuned with the physical low natural frequency of the handpiece (and possibly the needle).

Yet another embodiment of the present invention envisions a phacoemulsification configuration comprising a dual frequency voltage producing circuit comprising a low-frequency voltage pathway that includes a low-frequency oscillator and a low-frequency LC network and a high-frequency voltage pathway that includes a high-frequency oscillator and a high-frequency LC network. A hollow phacoemulsification needle extends from a handpiece wherein the handpiece including a piezoelectric crystal transducer. The piezoelectric crystal transducer is electrically connected to the dual frequency voltage producing circuit. When the high-frequency oscillator is in a high-frequency on state and the low-frequency oscillator is in a low-frequency off state, the hollow phacoemulsification needle comprises a single non-displacement region that has essentially no vibration displacement. When the low-frequency oscillator is in a low-frequency on state and the high-frequency oscillator is in an off state, the hollow phacoemulsification needle does not comprise a single non-displacement region.

Still yet, another embodiment of the present invention contemplates a method for driving a phacoemulsification assembly. The phacoemulsification assembly comprising a dual frequency producing circuit electrically connected to a phacoemulsification assembly comprising a phaco needle extending from a handpiece. The handpiece comprising a piezoelectric crystal transducer. The steps can include generating one of an independent high-frequency ringing in the phaco needle, an independent low-frequency ringing in the phaco needle or a combination high-low frequency ringing in the phaco needle. The high-frequency ringing is produced by energizing the piezoelectric crystal transducer with a high-frequency voltage from the dual frequency producing circuit. The high-frequency ringing generates a high-frequency standing wave comprising a single node of minimum amplitude that is along the phaco needle. The low-frequency ringing is produced by energizing the piezoelectric crystal transducer with a low-frequency voltage from the dual frequency producing circuit. The low-frequency ringing generates a low-frequency standing wave that is devoid of any node of minimum amplitude along the phaco needle at the low-frequency ringing.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving eye surgery. The phrases "in one embodiment", "according to one embodiment", and the like generally mean the particular feature, structure, or characteristic following the phrase is included in at least one embodiment of the present invention, and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". In what follows, similar or identical structures may be identified using identical callouts.

Described herein are phacoemulsification device embodiments configured to ultrasonically vibrate a phacoemulsification needle to advantageously fragment and emulsify a cataractous lens of a human eye. Generally speaking, described below is a surgical instrument is directed to phacoemulsification for cataract eye surgery. The instrument generally includes a dual frequency voltage producing circuit comprising a low-frequency voltage pathway with a low-frequency LC Network and a high-frequency voltage pathway with a high-frequency LC network. A phacoemulsification needle extends from a handpiece able to be driven by a piezoelectric crystal transducer. The piezoelectric crystal transducer is electrically connected to the dual frequency voltage producing circuit. The high-frequency voltage pathway is electrically tuned with the physical high natural frequency of the handpiece and the low-frequency voltage pathway is electrically tuned with the physical low natural frequency of the handpiece for efficient transfer of energy to the phaco needle.

Figure 1:
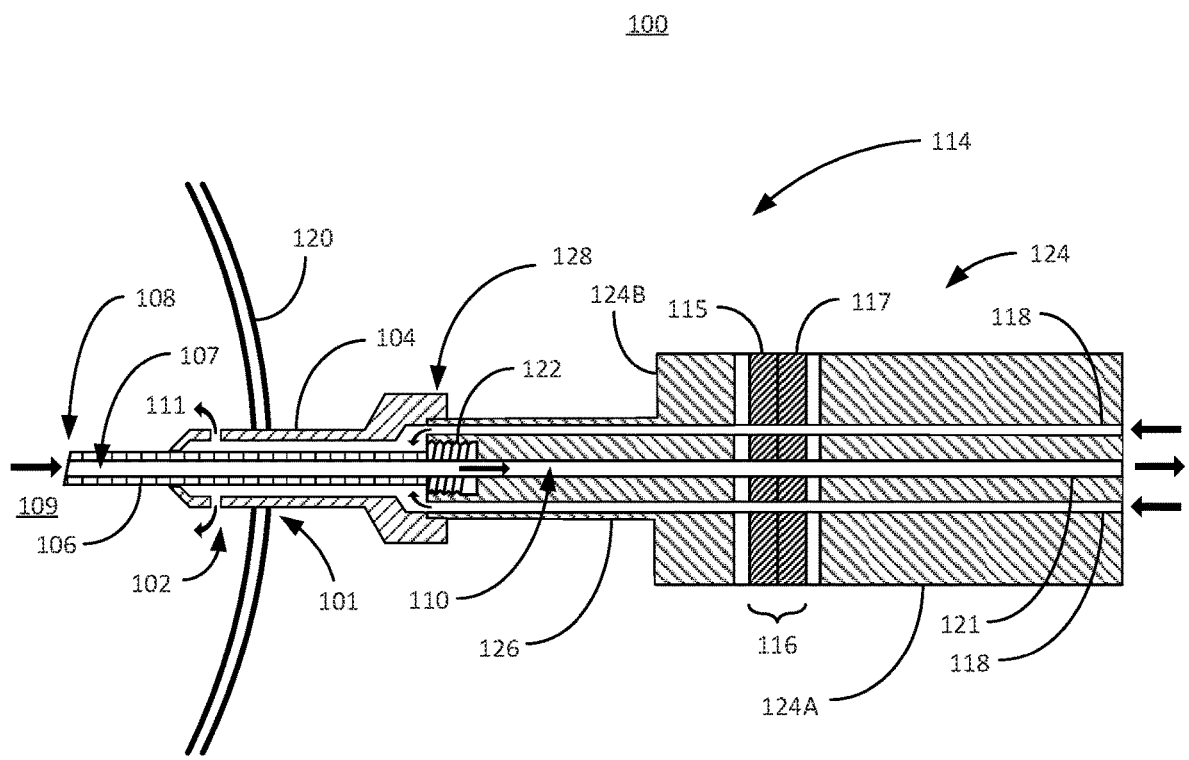
FIG. 1 illustratively depicts a line drawing of a phacoemulsification device embodiment inserted in an eye, the embodiment consistent with embodiments of the present invention.

FIG. 1 is a cross-section view line drawing of a phacoemulsification device embodiment inserted in an eye consistent with embodiments of the present invention. As depicted, the phacoemulsification device embodiment 100 generally comprises a handpiece 114, an aspiration needle 106 that extends from the handpiece 114, an irrigation sleeve 104 that concentrically surrounds a portion of the aspiration needle 106 (also known as a phacoemulsification needle or needle), and at least one irrigation port 102 extending through the irrigation sleeve 104.

During an ultrasonic phacoemulsification surgical procedure, a cataractous lens may be broken into particles by the combined cavitation effects and cutting action of the ultrasonically vibrating free distal tip 108 of needle 106. The vibration improves penetrating the needle 106 into lens tissue, while the cavitation of surrounding ocular liquid/fluid helps to emulsify or otherwise disintegrate lens tissue into small particles that can be aspirated through a narrow tube 107 (also known as an aspiration passageway) in the needle 106. Cavitation occurs because of rapid compression and expansion along the longitudinal axis of the phacoemulsification needle 106 at or near the free distal tip 108 thereby generating longitudinal waves in the surrounding ocular fluid. Unlike torsional and shear waves, longitudinal waves propagate well in fluids.

In the present embodiment, a back cylinder 124 and a front cylinder 126 define the handpiece 114. A pair of piezoelectric crystals 115 and 117 (together 116) are sandwiched between a front rear cylinder portion 124B and a back rear cylinder portion 124A that collectively make up the rear cylinder 124. The pair of piezoelectric crystals 115 and 117 are connected through a central bolt (not shown). Certain embodiments described herein may identify the piezoelectric transducer 116/124 as including the rear cylinder 124 and the piezoelectric crystals 116. As shown, the needle 106 is attached to the handpiece 114 at the supported end 128 via a supported end structure 122 that includes external threads that mate with internal threads in the handpiece 114. The needle 106 possesses a substantially cylindrical portion between the supported end structure 122 and the free distal tip 108. Substantially cylindrical defined herein is that the needle 106 may not be a perfect cylinder, but rather may be something between a cylinder to a slight taper (such a taper under 5%, for example) with the diameter of the needle 106 at the supported end structure 122 being larger than at the needle free distal tip 108. Moreover, the needle 106 may not be perfectly circular. In an embodiment, the needle 106 may be titanium or any other suitable material known in the art. The needle 106 comprises an aspiration passageway 107 that aligns with a handpiece aspiration passageway 121 forming a contiguous aspiration passageway 110. As ocular fluid and broken up cataract 109 are sucked through the aspiration passageway 110, replacement fluid 111 is transported along an infusion/irrigation pathway 118 and infused in the eye 120 via the irrigation ports 102 to prevent the eye 120 from collapsing.

One embodiment of the handpiece 114 envisions the back cylinder 124 possessing an outer diameter that is in a range between 9.5 mm and 13 mm. In some configurations, the front and rear back cylinder portions 124B and 124A are (more or less) comprised of stainless steel, but could just as easily be comprised of another suitable material, e.g., titanium, known to those skilled in the art. The handpiece 114 may also optionally include a front cylinder 126 that may have a front cylinder outer diameter that is preferably in the range 3.5 mm to 6.5 mm. In this case, the piezoelectric transducer 116/124 is preferably disposed between the rear back cylinder portion 124A and the front cylinder 126.

Figure 2:
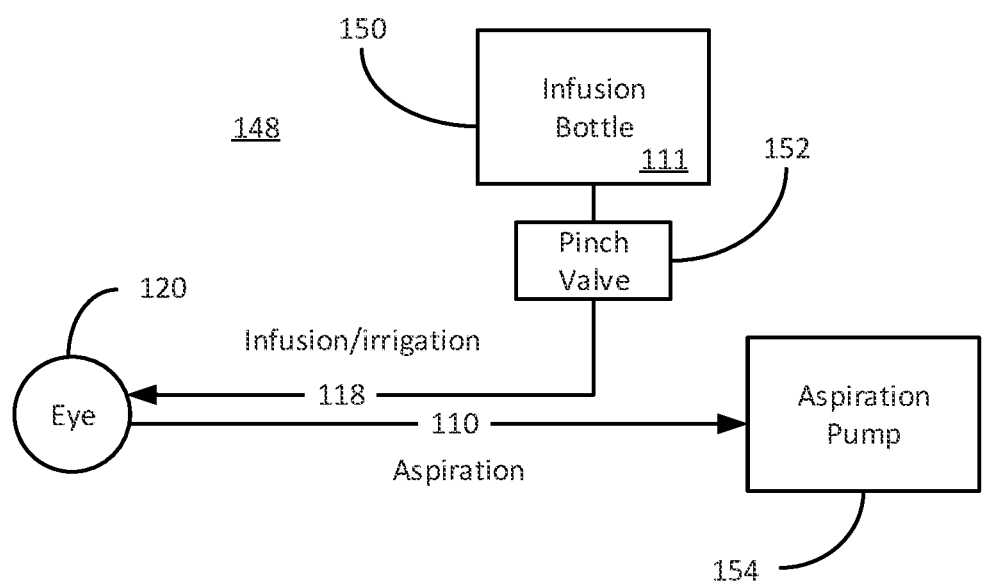
FIG. 2 is a block diagram of a phacoemulsification system embodiment consistent with embodiments of the present invention.

With reference to FIG. 2 in conjunction with FIG. 1, a block diagram of a phacoemulsification system embodiment 148 is presented consistent with embodiments of the present invention. As shown, the phacoemulsification system 148 includes an infusion bottle 150 filled with balanced salt solution (irrigation fluid) 111 that is generally positioned between 100 cm to 130 cm above the eye 120, or to a level that gravitationally provides balanced intraocular pressure (TOP) in the eye 120. In an embodiment, a pressurized fluid source may be employed in addition to or in the alternative to infusion bottle 150. IOP is generally between 10 mm Hg and 20 mm Hg and averages to 15.5 mm Hg in a human eye. During a cataract surgery, a surgeon tries to keep the IOP above 20 mm Hg, especially after a vacuum surge. Osmotically balanced salt solution is compatible with the ocular fluid in the eye 120. The system 148 further comprises a pinch valve 152 that opens and closes an infusion/irrigation pathway 118 to the eye 120. An aspiration pump 154 sucks or otherwise pulls emulsified lens/ocular material 109 from the eye 120 through the hollow opening in the free distal tip 108 of needle 106. During a phacoemulsification procedure, the aspiration needle 106 is inserted through an incision 101 in the anterior chamber of the eye 120 (at the cornea) up to and including the irrigation port 102. One embodiment contemplates the needle 106 vibrated at either an ultrasonic frequency or at a high ultrasonic frequency to break up (emulsify) lens material in the eye 120. Ultrasonic frequency as described herein is defined as a frequency below 60 kHz, and high ultrasonic frequency is defined herein as a frequency equal to or above 60 kHz. The small pieces of the emulsified lens material/an ocular fluid 109 are sucked through the needle 106 away from the eye 120 along the aspiration passageway 110 by way of a vacuum generated by the aspiration pump 154. The aspiration pump 154 is configured to pull (vacuum) a specific volume of emulsified lens material at a particular rate from the eye 120. Generally, the aspiration rate is approximately 25 to 50 cc of fluid/minute. Irrigation fluid 111 replaces the removed lens material (at the same particular rate of aspirated lens material) by way of gravity from the infusion bottle 150 that is raised at an appropriate distance above the eye 120 to maintain IOP. The irrigation fluid 111 flows and is discharged into the inside of the eye 120 through the irrigation port(s) 102 while the irrigation ports are located inside of the eye 120. In other words, the irrigation fluid 111 replaces the aspirated lens and ocular material 109 at the same rate at which the lens and ocular material 109 is removed from the eye 120 to maintain appropriate IOP, thus avoiding collapse of the anterior chamber of the eye 120. Hence, the irrigation flow rate into the eye 120 essentially equals the aspiration flow rate from the eye 120. The word essentially is used here to indicate that at some level, the flow rate is not exactly equal, but for all intents and purposes the two flow rates are more or less equal. The irrigation port 102 is an aperture or pathway into the irrigation sleeve 104, whereby irrigation fluid 111 passes from inside of the irrigation sleeve 104 out through the irrigation port 102 and into the eye 120. The irrigation sleeve 104 is spaced apart from the needle 106 thereby forming an irrigation pathway 118 over the needle 106, as shown. The irrigation pathway 118 extends from the infusion bottle 150, through the handpiece 114 to the irrigation port 102.

The effectiveness of a surgical instrument for phacoemulsification depends on the rate at which tissue is removed, which may be substantially affected by cavitation since cavitation may reduce partial or total occlusions of the needle 106. On the other hand, cavitation can cause a larger particle that is not readily sucked up through the free distal tip 108 to be pushed/chased away from the vibrating needle 106. Likewise, a larger particle may not sufficiently disintegrate to be aspirated away and simply shake off of the free distal tip 108 and get pushed/chased away from the vibrating needle 106. Either way, the surgeon may lose the particle and have to spend time maneuvering around the eye 120 to reengage the particle in order to suck it away. Hence, it is desirable to retain tissue particles once engaged with the needle 106. This is referred to as "followability." Followability is generally controlled and even enhanced by reducing cavitation during phacoemulsification.

One way to reduce cavitation is to excite the needle 106 to vibrate torsionally rather than longitudinally, so that the free distal tip 108 alternately rotates clockwise and counterclockwise in relation to its longitudinal axis. Torsional vibrations do not readily propagate as waves in fluid, so that cavitation effects are substantially reduced. However, a free distal tip 108 that is vibrating purely torsionally may too easily core into the eye's lens material without sufficient disintegration of tissue into particles, which consequently, may disadvantageously lead to total occlusions in the needle 106.

According to one embodiment of the present invention, followability may be enhanced by longitudinally ringing needle 106 at a carefully selected and substantially higher frequency than has been used previously for phacoemulsification. In some embodiments, the ringing frequency is chosen so that the phacoemulsification needle length corresponds to an approximately three-quarter vibration wavelength. Such a higher ultrasonic frequency, in combination with the proper length of the needle 106, leads to reduced heating of tissue at the incision 101 in the cornea. This is considered a 'cold needle' herein and will generate a larger quantity of smaller sized cavitation bubbles per unit volume. The energy delivered by a cavitation bubble is related to the bubble radius, which is inversely related to the frequency of vibration. Hence, a higher ultrasonic frequency generates smaller cavitation bubbles than a lower ultrasonic frequency. For example, a bubble generated by a 40 kHz wave may be approximately 41 µm in diameter, yet at 215 kHz a bubble size may have a diameter of approximately 7.6 µm. When a greater quantity of smaller bubbles is generated, cavitation patterns are more uniformly distributed over the cutting area as compared with fewer larger bubbles. One of the results is enhanced followability compared with a phacoemulsification needle operating at conventional longitudinal ultrasonic vibrations.

Figure 3A:
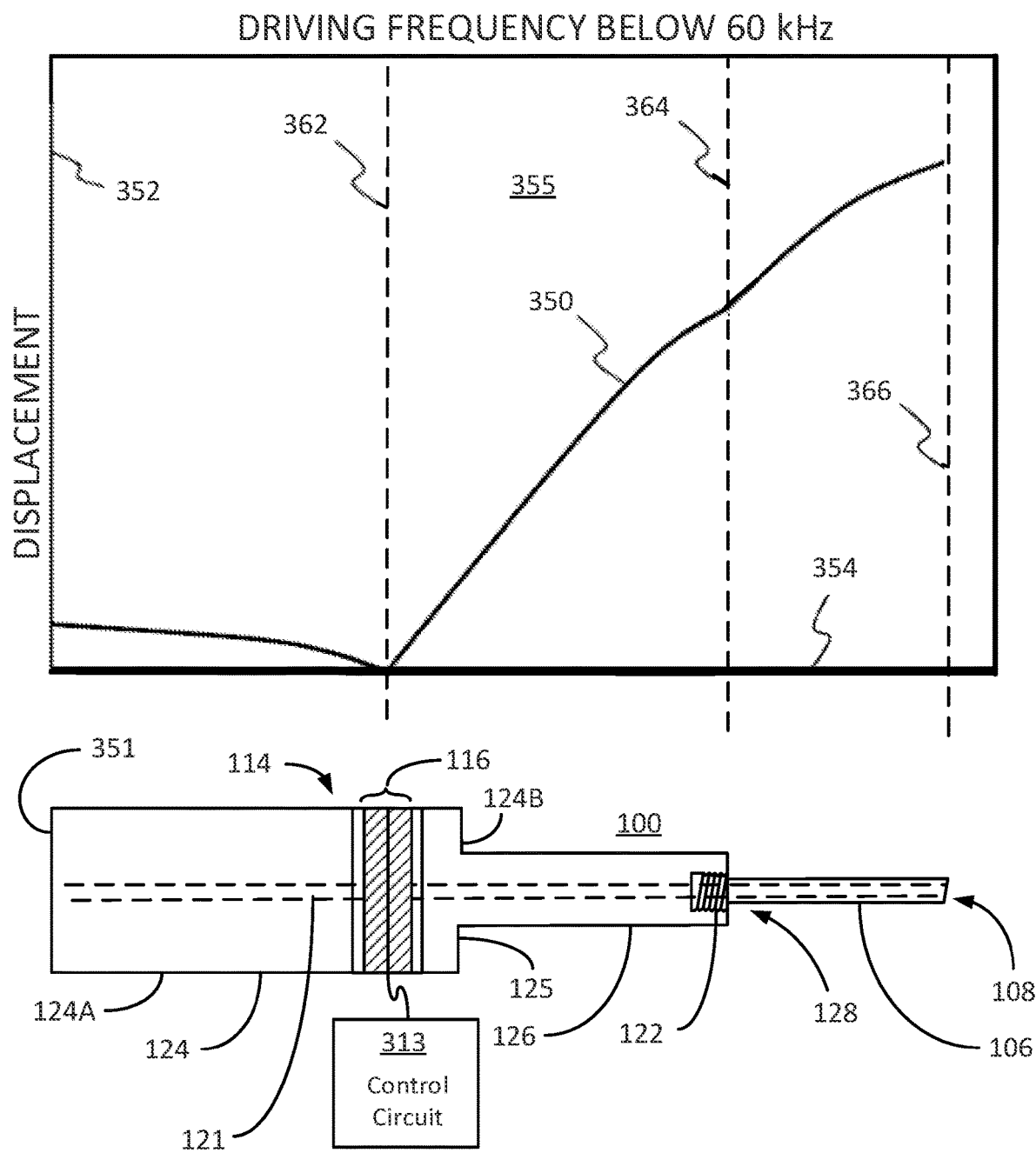
FIG. 3A is a line drawing of an ultrasonic frequency response plot aligned with a handpiece and hollow needle embodiment consistent with embodiments of the present invention.

FIG. 3A is a line drawing of an ultrasonic frequency response plot aligned with a handpiece and needle embodiment 100 (the phacoemulsification assembly) consistent with embodiments of the present invention. As shown, this is a vibration amplitude standing wave plot in relation to (along) the length of a handpiece 114 and needle 106 wherein the handpiece is generating longitudinal vibrations operating at an (low) ultrasonic frequency below 60 kHz. Consistent with FIG. 1, the handpiece 114 includes a back cylinder 124 and a front cylinder 126 comprising a pair of piezoelectric crystals 116 sandwiched via a central bolt (not shown). Some embodiments contemplate four or six piezoelectric crystals or more. A control feedback circuit 313 (shown in detail in FIG. 3B) connects to the piezoelectric transducer 116/124 to provide an oscillating voltage that drives the piezoelectric crystals 115 and 117. The wavelength λ of a longitudinally ringing phacoemulsification device is defined by λ=c/f, where c is the speed of sound through the structure's material and f is the frequency of operation. The speed of sound in titanium material is approximately 4,876,800 mm/sec. Accordingly, the needle 106 longitudinally vibrating at a frequency of 40 kHz (40000 Hz) has a wavelength of (4,876,800 mm/s)/(40,000 Hz)=122 mm.

In FIG. 3A, the combined length of the front cylinder 126 and the back cylinder 124 is approximately ½ the wavelength during conventional ultrasonic operation, with a node of zero vibration amplitude at a location 362 at the interface between the two piezoelectric crystals 115, 117. For that reason, the handpiece 114 may be referred to as a "half-wavelength horn."

Figure 3B:
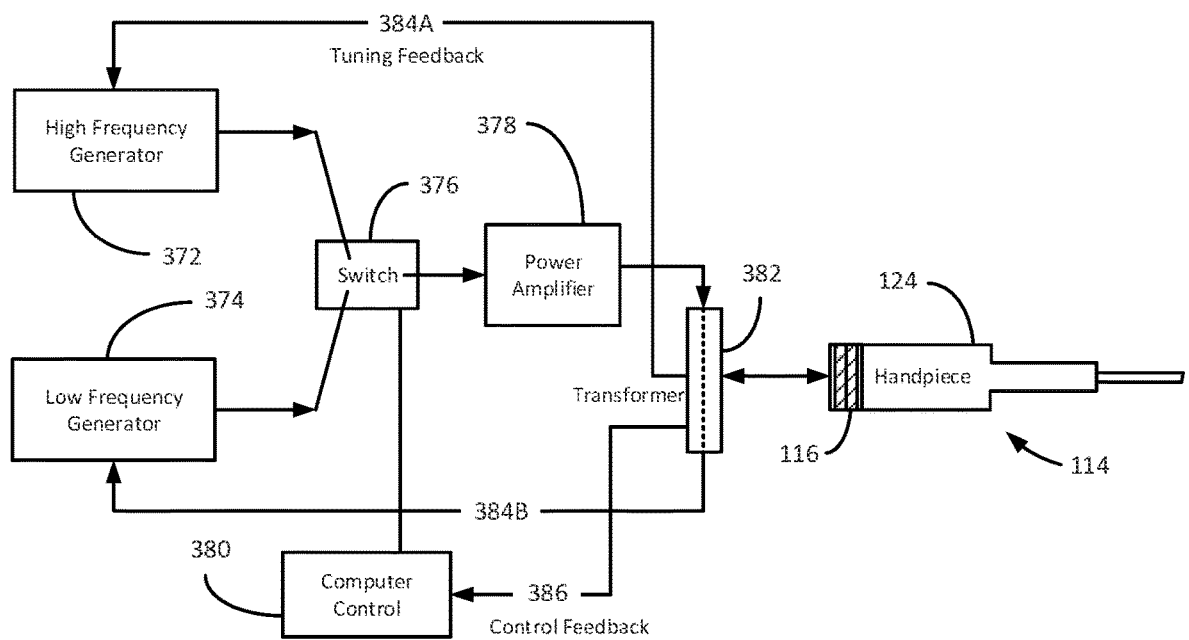
FIG. 3B is a block diagram layout of an embodiment of a control feedback circuit for a phacoemulsification device consistent with embodiments of the present invention.

FIG. 3B is a block diagram of a control feedback circuit embodiment 313 that provides an oscillating voltage to the piezoelectric transducer 116/124. As generally shown, a high frequency generator 372 provides high ultrasonic frequency voltage input to the piezoelectric transducer 116/124 in the handpiece 114 and a low frequency generator 374 provides a low (or regular) ultrasonic frequency voltage input to the piezoelectric transducer 116/124 in the handpiece 114. In this embodiment, a switch 376 directs either the high or low ultrasonic frequency voltage to the power amplifier 378 and a transformer 382. More specifically, a computer controller 380 sends signals to modulate input from either the high frequency generator 372 or the low frequency generator 374, wherein that signal (from one of the generators 372, 374) passes through the switch 376. The switch 376 selected voltage is amplified by the power amplifier 378 and then translated to the two piezoelectric crystals 115, 117 via the transformer 382 to drive the needle 106 with the selected frequency wave. The transformer 382 is arranged to detect slight impedance changes, or resonance mismatches, between the piezoelectric transducer 116/124 and the circuit 313. In this embodiment, those impedance changes are communicated to the high frequency generator 372 and low frequency generator 374 along the tuning feedback loops 384A and 384B, respectively. Accordingly, the frequencies generated by the high frequency generator 372 and/or the low frequency generator 374 are adjusted to more closely match the resonance of the handpiece 114. Also in this embodiment, feedback from the transformer 382 along control feedback 386 facilitates switching between the signals produced by the high frequency generator 372 or the low frequency generator 374 via the computer controller 380. Optional embodiments contemplate the computer controller 380 blending the high frequency and low frequency signals in a desired proportion. In this way, by sensing increased loading to the system, e.g., an engaged particle occluding the free distal tip 108 of needle 106, the computer controller 380 can be made to toggle the switch 376 (or vice versa if the particle is no longer engaged with the needle 106) via a controlling algorithm, for example.

The phacoemulsification assembly 100 of FIG. 3A is not drawn to scale, so that the needle 106 may be more clearly depicted as a hollow cylinder. In this embodiment, the needle 106 is attached to the handpiece 114 using supported end structure 122 having threads, however other attachment embodiments known to those skilled in the art can be readily employed without departing from the spirit of the present invention. One embodiment contemplates the length of the needle 106 having a small cross-sectional area with a length that is less than a ¼ wavelength (30.5 mm at 40 kHz), for example 17 mm. The mass of the needle 106 is also small when compared with the mass of the handpiece 114. Consequently, the needle 106 does not dramatically change the dynamic resonance characteristics of the handpiece 114. As discussed previously, the needle 106 includes a narrow tubular passage 107 there through. The tubular passage 107 contiguously connects to the handpiece aspiration passageway 121 forming the uninterrupted aspiration passageway 110 so that fluid and tissue can be aspirated through the needle 106 to aspiration tubing (not shown) that is connected to the handpiece 114. The aspiration tubing is linked to a pump 154 that provides sub-ambient pressure to the aspiration passageway 110 in the handpiece 114 to suck/aspirate lens and ocular material 109 from the eye 120.

The cross-sectional area of the front cylinder 126 of the handpiece 114 is smaller than the cross section area of the back cylinder 124, in order to generate the displacement magnification as shown by the standing wave plot 350 above the phacoemulsification device, as shown in FIG. 3A. Specifically, the displacement at the rightmost extent 364 of the front cylinder (step horn) 126 may be approximately 20 times the displacement at the leftmost edge (proximal handle end 351) of the rear cylinder 124 and the front cylinder (step horn)/rear cylinder interface 125. Note that the vertical axis 352 of the graph 355 represents displacement amplitude (longitudinal compression and expansion increasing upwards). The horizontal axis 354 of the graph 355 represents the longitudinal coordinate along the length of the handpiece 114 and needle 106. Longitudinal strain in the needle 106 marginally increases the displacement in the vertical direction as plotted in the vibration response 350, though the entire needle 106 longitudinally translates the vibration in the horizontal direction. In this example, the displacement at the location 366 of the free distal end 108 of the needle 106 is somewhat greater than the displacement at the rightmost extent 364 of the front cylinder 126. Note that there is no location of zero vibration (i.e. nodal point) along the length of the needle 106.

One embodiment contemplates the needle 106 being substantially cylindrical, with an outer diameter in the range 0.5 mm to 1.5 mm and a length in the range 12 mm to 37 mm, the length being defined along a longitudinal axis of the needle 106 (i.e. parallel to graph axis 354). In this context "cylindrical" does not necessarily mean cylindrical with a circular or annular cross section. Rather, any closed hollow extruded shape may be used (e.g. a closed hollow square cross-section). However, an annular cross-section having circular inner and outer peripheries may be preferred for manufacturability.

Figure 4:
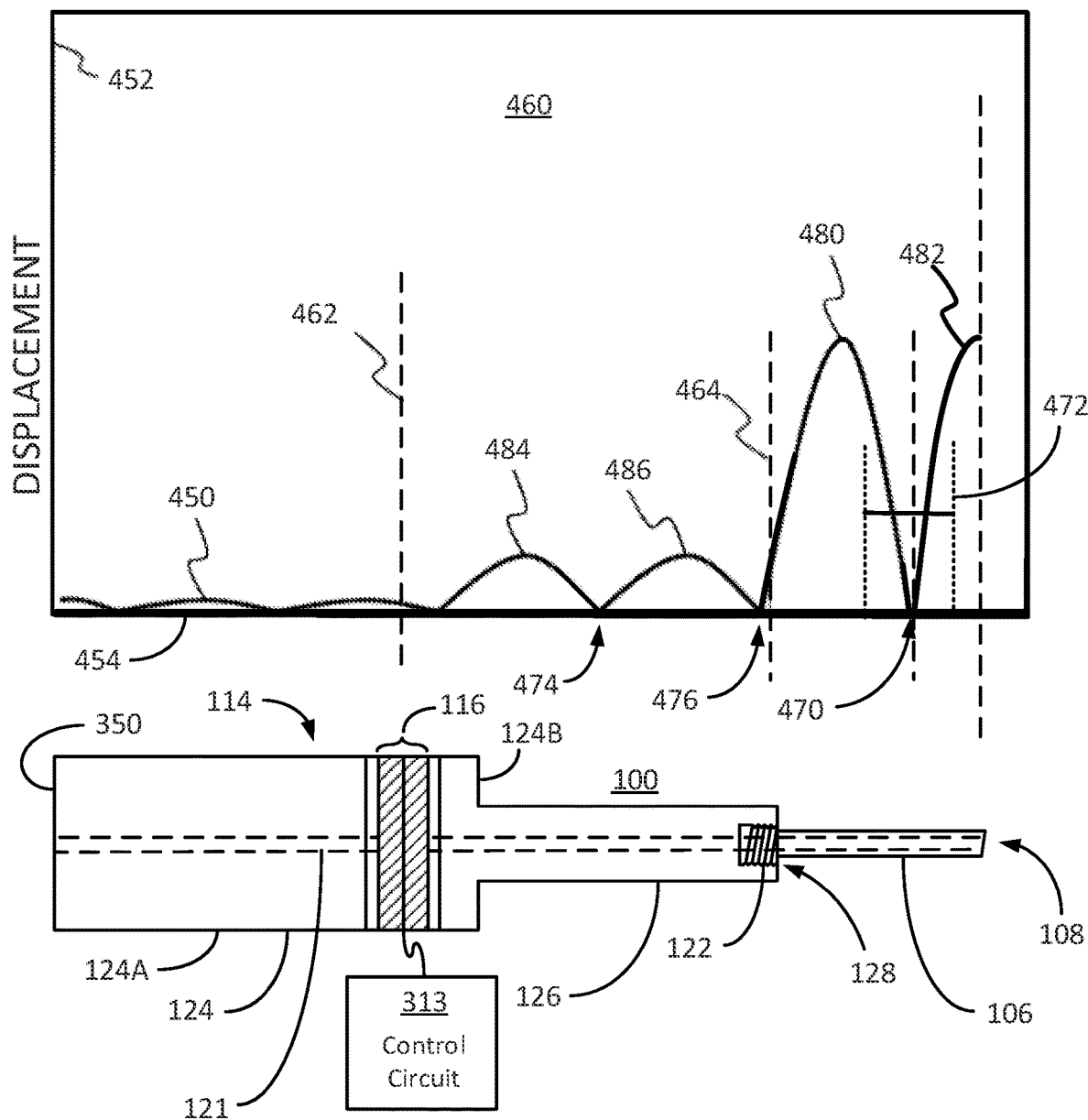
FIG. 4 is a line drawing of a high ultrasonic frequency response plot aligned with a handpiece and hollow needle embodiment consistent with embodiments of the present invention.

FIG. 4 is a line drawing of a high ultrasonic frequency response (standing wave) plot aligned with a handpiece and needle embodiment 100 consistent with embodiments of the present invention. FIG. 4 depicts the phacoemulsification assembly 100 of FIG. 3A whereby the handpiece 114 is ringing the needle 106 at a high ultrasonic frequency, equal to or above 60 kHz. As previously described, the handpiece 114 includes a piezoelectric transducer 116/124, wherein the piezoelectric transducer 116/124 comprises a sandwich structure of two piezoelectric elements 115, 117, which meet at an interface location 462 in-between the front and rear back cylinder portions 124B and 124A. The piezoelectric crystals 115, 117 may comprise piezoelectric ceramics or crystals, preloaded to be in compression by a bolt in tension, for example.

The front cylinder 126 may also be substantially made out of titanium, for example, to match the speed of sound of the titanium needle 106 and thereby reduce acoustic reflections at the interface between the front cylinder 126 and the needle 106.

The surgical instrument depicted in FIG. 4 includes the circuit 313 that controls an oscillating voltage to the piezoelectric transducer 116/124 in the handpiece 114. The voltage oscillating at a driving frequency that rings the needle 106 at different ultrasonic frequencies with corresponding standing waves characterized by longitudinal expansion and longitudinal contraction. In certain embodiments, the high frequency (generated from the high frequency generator 372) with which the control feedback circuit 313 drives the piezoelectric transducer 116/124 is preferably in a range above 100 KHz. Optional embodiments envision the high frequency being above 60 KHz and the low frequency (generated by the low frequency generator 374) being below 60 KHz. For example, in this embodiment, the total length of the needle 106 may be approximately 17 mm, and the driving frequency may optionally be equal to or above 60 KHz. Higher frequencies may introduce additional nodal waves along the length of the titanium needle 106.

Such dimensional ranges and driving frequencies may advantageously result in ¾ wavelengths of the longitudinal standing wave lying along the needle 106, such as if it is a titanium needle of 17 mm total length, for example. This can be verified by referring again to the formula $\lambda = c/f$. Specifically, according to this formula the wavelength of the standing longitudinal wave in a titanium needle in this configuration is (4,876,800 mm/s)/215,000 Hz)=22.7 mm. Hence, the ¾ wavelength would proportionally lie along a needle having a length of 17 mm.

An example of the amplitude of the longitudinal expansion and contraction causing displacement along the handpiece 114 and the needle 106, according to an embodiment of the present invention, is plotted with a standing wave 450 versus longitudinal position in the graph 460 that is aligned above the handpiece 114 in FIG. 4. The vertical axis 452 of the graph 460 represents displacement amplitude (increasing upwards). The displacement amplitude in the graph 460 is dimensionless. The horizontal axis 454 of the graph 460 represents the longitudinal coordinate along the length of the handpiece 114 and the needle 106.

In the embodiment of FIG. 4, the standing wave plot 450 shown in graph 460 preferably has a distal node of minimum amplitude at a node location 470 on the substantially cylindrical needle 106 between the free distal tip 108 and the supported end 128. This is depicted on the standing wave plot 450 as a minimum point at the node location 470. Unlike ultrasonic vibrations in a range under 100 kHz (e.g. like that shown in FIG. 3A), the portion of the needle 106 that is most likely to contact the incision 101 in the cornea, will be in a corneal contact region 472. The corneal contact region 472 includes a minimum node 470 in the standing vibration wave 450, which exhibits significantly lower motion than does the free distal tip 108 (i.e., this is a 'cold needle' region 472). In certain embodiments, the 'cold needle' region 472 may advantageously reduce heating of the tissue at and near the incision 101 (of FIG. 1) in the cornea when this 'cold needle' region 472 of the needle 106 interfaces the incision 101.

With continued reference to FIG. 4, the standing wave plot 450 has a proximal node of minimum amplitude 476 near or adjacent the supported end 128. This is depicted as a minimum point on the standing wave plot 450, just to the left of line 464, which corresponds to the supported end 128 of front cylinder 126. Note that the proximal node of minimum amplitude 476 is not the same as the distal node of minimum amplitude at node location 470, and of course does not serve as a 'cold needle' region 472. Here, the standing wave 450 may have a distal anti-node 482 of maximum amplitude at or near the free distal tip 108 thereby enhancing tissue penetration by the free distal tip 108. The constant thickness of the needle 108 responds with a vibration peak essential equal for anti-nodes 480 and 482.

Other nodes (e.g. node 474) may exist in the displacement amplitude graph along the front cylinder 126, but these are not the same as the distal node at node location 470, nor do they serve the same purposes as described for the distal node at node location 470. Another anti-node 480 may exist in the substantially cylindrical portion of the needle 106, but it does not serve the same purpose as does the distal anti-node 482 of maximum amplitude at the free distal tip 108. However, in certain embodiments, the existence and location of the anti-node 480 is an expected consequence of the desired placement of the distal node of minimum amplitude 470. Other anti-nodes (e.g. anti-nodes 484, 486) may exist in the displacement amplitude graph along the front cylinder 126, but these are not the same as the distal anti-node 482 of maximum amplitude at the free distal tip 108, nor do they serve the same purpose as does the distal anti-node 482 of maximum amplitude at the free distal tip 108.

Certain embodiments of the present invention contemplate switching the applied vibration frequency to the needle 106 between ultrasonic frequency and high ultrasonic frequency. As previously discussed, at high ultrasonic frequency there is a node of minimum amplitude 470 along the substantially cylindrical portion of the needle 106 between the distal free end 108 and the supported end 128 whereby near or at the distal node of minimum amplitude 470 there is little to no heat generated. As previously discussed, this is considered a 'cold needle'. Also as previously discussed, the control feedback circuit 313 is configured to modulate, or change, the frequency between the ultrasonic frequency and high ultrasonic frequency.

Certain embodiments contemplate a routine (either in hardware or in software) that causes the control feedback circuit 313 to modulate frequencies driving the needle 106 between the ultrasonic frequency and high ultrasonic frequency after a predetermined time interval. One embodiment envisions the frequency modulating between ultrasonic frequency and high ultrasonic frequency over a predetermined amount of time that is symmetrical or otherwise equal for high and low ultrasonic frequencies. For example, after every 5 seconds (or some other amount of time) the control feedback circuit 313 drives the hollow titanium needle 106 from the ultrasonic frequency to the high ultrasonic frequency and then back again. Yet another example includes causing the control feedback circuit 313 to change from ultrasonic to high ultrasonic in an asymmetric amount of time, such as for example, 5 seconds (or some other amount of time) at ultrasonic frequency then 3 seconds (or some other amount of time) at high ultrasonic frequency and then repeat. The predetermined amount of time is envisioned to be set either manually by someone in the operating room or default routines set by the manufacturer, just to name a couple of examples of how to set the time at each frequency. The software that controls the different frequencies can be executed via the computer controller 380 or equivalent computing device. Other embodiments contemplate manual intervention to modulate frequencies driving the needle 106 between the ultrasonic frequency and high ultrasonic frequency. One embodiment envisions a foot pedal or other manually operated switching device (or potentiometer) modulating the frequency between ultrasonic frequency and high ultrasonic frequency.

Figure 5:
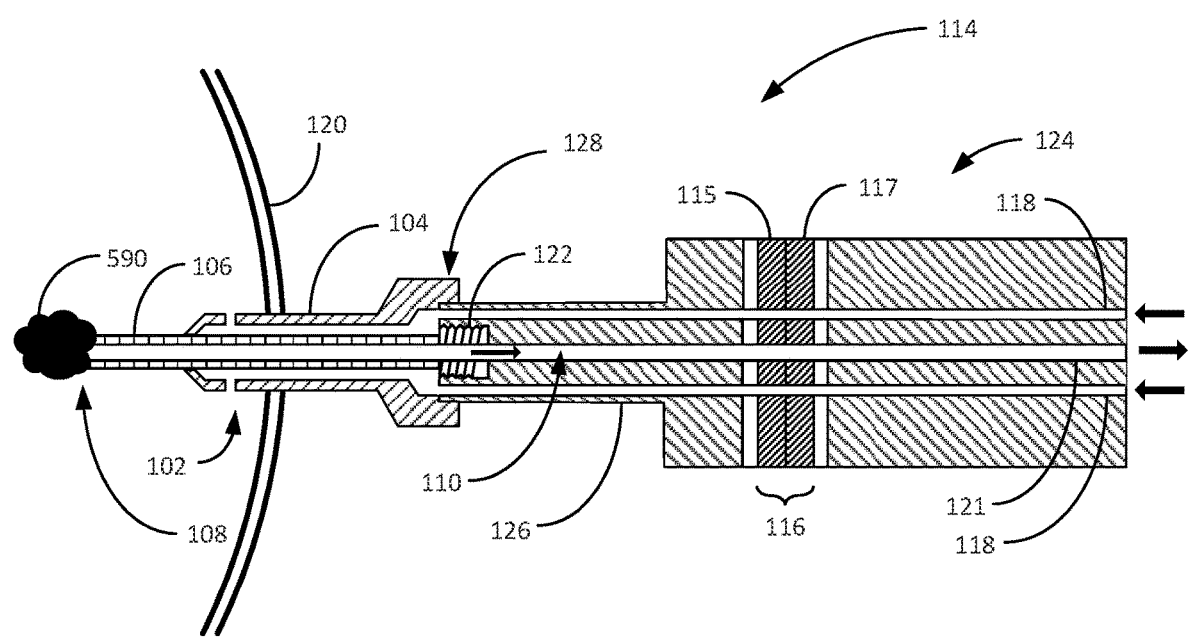
FIG. 5 illustratively depicts a line drawing of an occluding particle obstructing the aspiration passageway at the free distal tip of a hollow needle consistent with embodiments of the present invention.

Yet other embodiments contemplate managing an event during a phacoemulsification procedure that advantageously utilizes driving the needle 106 to modulate or otherwise shift between the ultrasonic and high ultrasonic frequency. For example, and with reference to FIG. 5, depicted is a particle 590, such as lens material, that is occluding the aspiration passageway 110 at the free distal tip 108 of the hollow titanium needle 106. When a particle 590 is engaged in such a way, it can decrease flow rate in an aspiration passageway 110. For example, with a peristaltic pump, the aspiration flow rate is always constant. The pump automatically increases vacuum to overcome an increased resistance to aspiration flow. If the occluded aspiration passageway 110 (such as from the particle 590) is not cleared by the pump's maximum vacuum/effort, the aspiration flow could drop to zero. In general, the aspiration flow rate is either constant or zero. With a Venturi type pump, the aspiration flow rate decreases or increases as a function of pipe resistance, which can be caused by an occlusion (such as from the particle 590). In either situation, the irrigation flow along pathway 118 is reduced or drops to zero to match the pump flow rate in order to maintain proper IOP. A reduction or stoppage of irrigation fluid 111 can cause localized heating at the cornea. In this situation, increasing the frequency of the needle 106 from ultrasonic to high ultrasonic can reduce localized heating at the incision site 101 (of FIG. 1) of the cornea and can help breakup the particle 590 to allow aspiration and irrigation to proceed normally at an unblocked flow rate.

Feedback in the phacoemulsification system 148 (of FIG. 2) to an occlusion or partial occlusion of the aspiration passageway 110 due to a particle 590 can trigger a routine that causes the needle 106 to modulate from the ultrasonic frequency to the high ultrasonic frequency (or optionally back and forth). Modulating between the ultrasonic frequency and the high ultrasonic frequency will likely break up the particle 590 and reduce heating at the corneal incision 101 during a phacoemulsification procedure. Some embodiments contemplate using feedback in the phacoemulsification system 148 to identify if a particle is engaged in an occluding or partial occluding manner. This can include a diminished aspiration flow rate of ocular material aspirated from an eye 120 causing a diminished irrigation flow rate of irrigation fluid into the eye 120 (to maintain balanced TOP), an increased aspiration vacuum (which could be based on how hard an aspiration pump 154 has to work to aspirate ocular material from the eye 120), or an increase in load to drive the frequency of the needle 106 due to an increased mass of a particle engaged/lodged in or on the free distal tip 108 of needle 106. Sensors can be employed to evaluate these aforementioned scenarios to initiate modulating the ringing frequency. For example, a sensor (not shown) can be located in the aspiration passageway 110 or irrigation pathway 118, or elsewhere, to sense a diminished flow rate of aspiration material from the eye 120 or irrigation fluid into the eye 120, given that these flow rates are intrinsically connected to maintain TOP. Similarly, the aspiration pump 154 can be used to sense an occlusion based on what is considered a normal resistance to flow. For example, back electro-magnetic force (EMF) of the pump is an effective way to identify if there is an occlusion in the aspiration passageway 110. When the aspiration ocular material is flowing at an expected flow rate that does not reflect an occluded or partially occluded aspiration passageway 110, the control feedback circuit 313 can be made to operate in a manner before the occlusion occurred. Some embodiments contemplate using the piezoelectric transducer 116/124 to identify the presence of a particle 590 based on an increase in mass of the needle 106 due to the particle 590 engaged therewith. An increase in the mass of the needle 106 due to the engaged particle can correspond to an increase in voltage load to drive the frequency via the piezoelectric transducer 116/124. When the mass of the needle 106 returns to a level that does not reflect an increased voltage level to drive the circuit, the system can return to the state before the occlusion occurred.

Certain optional embodiments contemplate employing frequencies ringing the needle 106 in a manner opposite to the above embodiments describing ultrasonic frequencies modulating to high ultrasonic frequencies. For example, generally ringing the needle 106 at a high ultrasonic frequency and then modulating the ringing to a lower ultrasonic frequency may improve breaking up an occluding particle 590 with cavitation. In this scenario, an occlusion may be cleared faster at a low ultrasonic frequency where larger bubbles are generated by increased cavitation effects.

Certain embodiments of the present invention contemplate ringing the needle 106 between the ultrasonic (low) frequency range (20 kHz to below 60 kHz) and a sonic frequency range (less than 20 kHz). A sonic frequency, or frequency that is in the sound range, greatly reduces the heating effects of vibration on the needle 106. A sonically vibrating needle 106 is also considered a 'cold needle' because there is little risk of burning the incision site 101 of the cornea. Much like the embodiments described herein that are directed to modulating the frequency ringing the needle 106 between an ultrasonic frequency and a high ultrasonic frequency, the same embodiments are further contemplated using the condition where sonic frequency is substituted in place of the high ultrasonic frequency. In other words, some embodiments are further envisioned to modulate the needle 106 from ultrasonic frequency to sonic frequency when there is an occlusion or partial occlusion, or optionally when a surgeon wants to manually switch between ultrasonic and sonic frequencies, or optionally toggling between the two after a predetermined amount of time, for example.

Certain embodiments of the present invention contemplate employing frequencies ringing the needle 106 in a manner similar to the above embodiments but with a substitution of modulating ultrasonic frequencies to sonic frequencies. For example, ringing the needle 106 at a sonic frequency and then modulating to an ultrasonic frequency to breakup an occluding particle 590.

Figure 6:
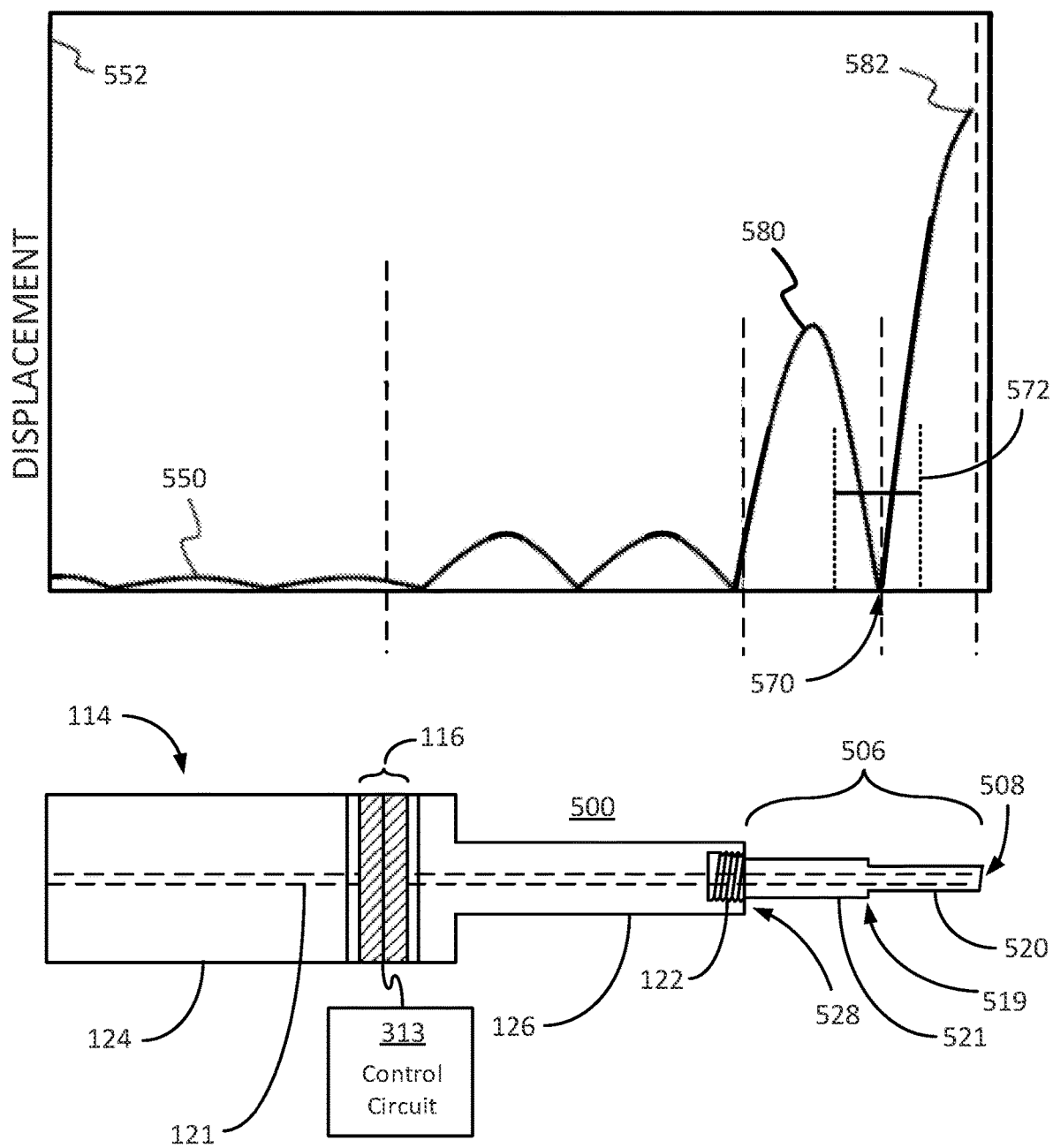
FIG. 6 is a line drawing of a high ultrasonic frequency response plot aligned with of an embodiment of a handpiece and hollow needle with a shoulder in the substantially cylindrical portion of the needle consistent with embodiments of the present invention.

Another optional embodiment is depicted in FIG. 6, which contemplates the needle 506 (which is hollow and may be titanium, or other suitable material known in the art) including a shoulder 519. The shoulder 519 is essentially a step that defines where the outer diameter of needle 506 changes from a larger diameter to smaller diameter. More specifically, the needle 506 includes a first substantially cylindrical portion 520 between the shoulder 519 and the free distal tip 508 and a second substantially cylindrical portion 521 between the shoulder 519 and the supported end 528. The first substantially cylindrical portion 520 is smaller in diameter than the diameter of the second substantially cylindrical portion 521. In this case, the shoulder 519 is preferably located between 5 and 8 mm from the free distal tip 508. The inequality of the diameters advantageously amplifies the ringing amplitude in the first substantially cylindrical portion 520 as illustratively depicted by the standing wave plot 550 of the needle 506 subjected to a high ultrasonic frequency equal to or above 60 kHz. In more detail, there is a distal node of minimum amplitude at a node location 570 on the substantially cylindrical needle 506 approximately at the shoulder 519. Accordingly, the needle 506 is considered 'cold' at or near the shoulder 519 because the needle 506 is not vibrating with a significant amplitude. Also, if the shoulder 519 is visible, a surgeon can readily see where the coolest part of the needle 506 is during surgery. The standing wave shown in graph 550 has a distal anti-node 582 of maximum amplitude at the free distal tip 508 (which has a peak higher than the amplitude of the anti-node 580 because the needle 506 possesses the smaller diameter of the first substantially cylindrical portion 520). The high displacement amplitude at distal anti-node 582 at the distal tip 508 enhances tissue penetration by the free distal tip 508 during operation.

In certain embodiments, the advantage of reduced corneal incision 101 heating may be obtained by the distal node of minimum amplitude 570 preferably located between 5-8 mm from the free distal tip 508. Although in the embodiment of FIG. 5 the shoulder 519 is depicted as being essentially at the distal node of minimum amplitude 570 this is not a requirement. Indeed, in certain embodiments it is preferred that the distal node of minimum amplitude 570 does not coincide or otherwise reside at the shoulder 519. For example, the distal node of minimum amplitude 570 may be located more distally towards the free distal tip 508 instead of essentially (such as +/−1 mm) at the shoulder 519.

Figure 7A:
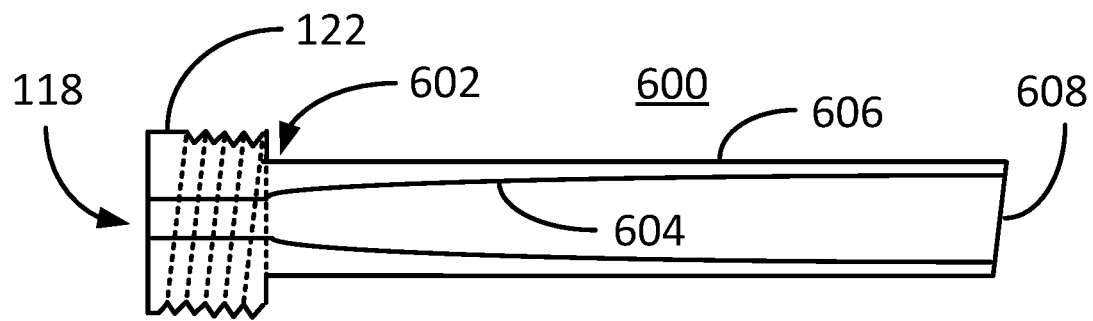
FIGS. 7A-7D illustratively depict line drawings of optional bore profiles in a hollow needle consistent with embodiments of the present invention.
Figure 7B:
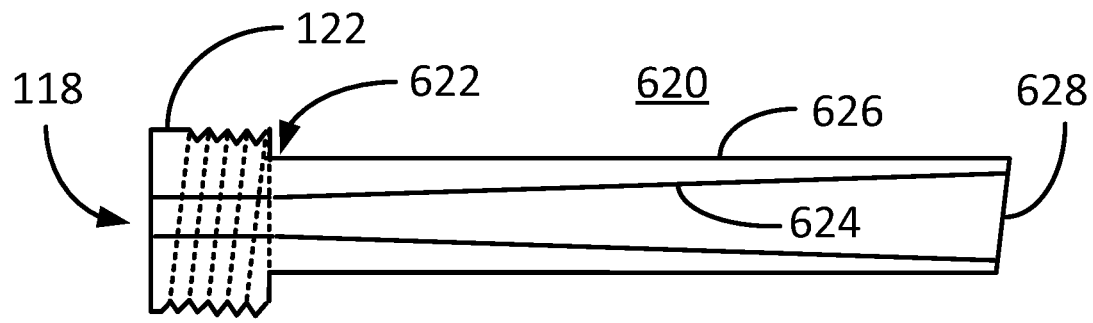
Figure 7C:
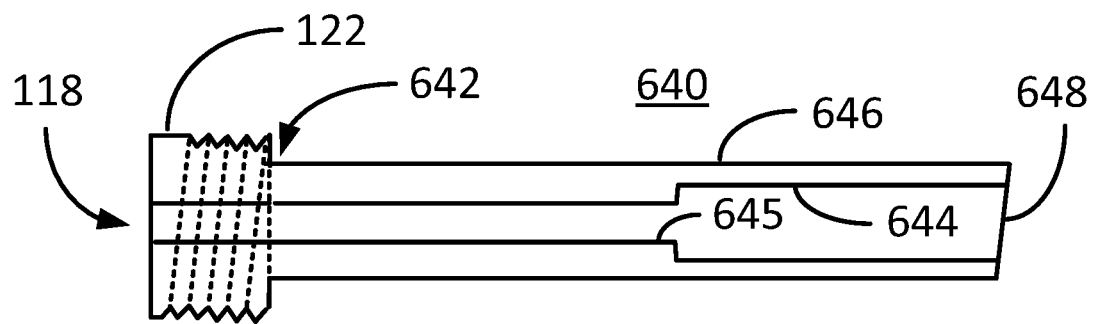
Figure 7D:
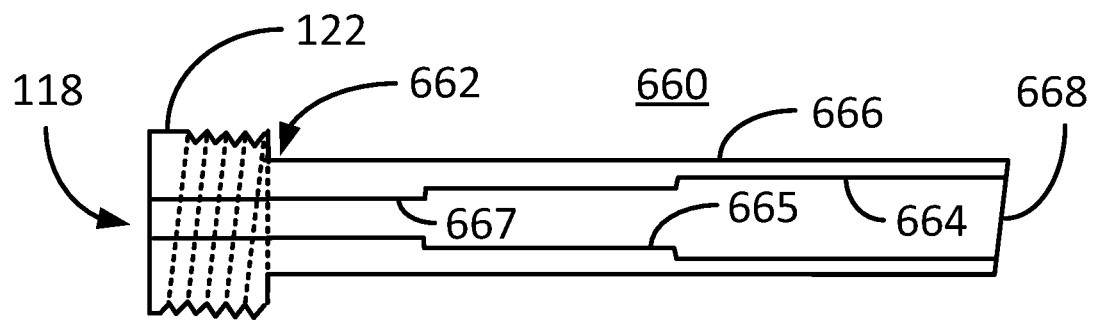

FIGS. 7A-7D are line drawings of alternate inner bore geometries that affect the vibration response of an ultrasonically driven needle consistent with embodiments of the present invention. FIG. 7A illustratively depicts a needle 600 (which is hollow and may be titanium, or other suitable material known in the art) comprising an elliptical shaped bore 604 that possesses a thicker needle wall as it approaches the supported end 602 and a thinner needle wall as it approaches the free distal tip 608. The outer needle diameter 606 is essentially constant or otherwise cylindrical between the supported end 602 and the free distal tip 608. FIG. 7B illustratively depicts another embodiment of a needle 620 (which is hollow and may be titanium, or other suitable material known in the art) comprising a linear angulated bore 624 comprising a thicker needle wall towards the supported end 622 and a thinner needle wall towards the free distal tip 628. The outer needle diameter 626 is essentially constant between the supported end 622 and the free distal tip 628. FIG. 7C illustratively depicts yet another embodiment of a needle 640 (which is hollow and may be titanium, or other suitable material known in the art) comprising an internal stepped bore 644, 645 that possesses a thicker needle wall along bore 645 proximal to the supported end 642 that steps to a thinner needle wall along bore 644 as it approaches the free distal tip 648. The outer needle diameter 646 is essentially constant between the supported end 642 and the free distal tip 648. FIG. 7D illustratively depicts yet another embodiment of a needle 660 (which is hollow and may be titanium, or other suitable material known in the art) comprising an internal stepped bore 664, 665, and 667 comprising a needle wall along bore 667 that is thickest proximal to the supported end 662, that steps down to an intermediate thickness wall along bore 665 in the middle of the needle 660, with another step to a thinner needle wall along bore 664 towards the free distal tip 668. The outer needle diameter 666 is essentially constant between the supported end 662 and the free distal tip 668. Though the bore 645 in FIG. 7C and the bores 665 and 667 in FIG. 7D have thicknesses that are essentially parallel to the outer diameter 666 of the needle 660, certain embodiments contemplate such a condition not being required. For example, the thicknesses can be tapered, curved, etc., within the scope of different thickness bores. Moreover, the different thickness bores may be implemented to alter the frequency profile to create nodes of minimum amplitude or create varied frequency responses at specific locations along the length of the needle.

Figure 8:
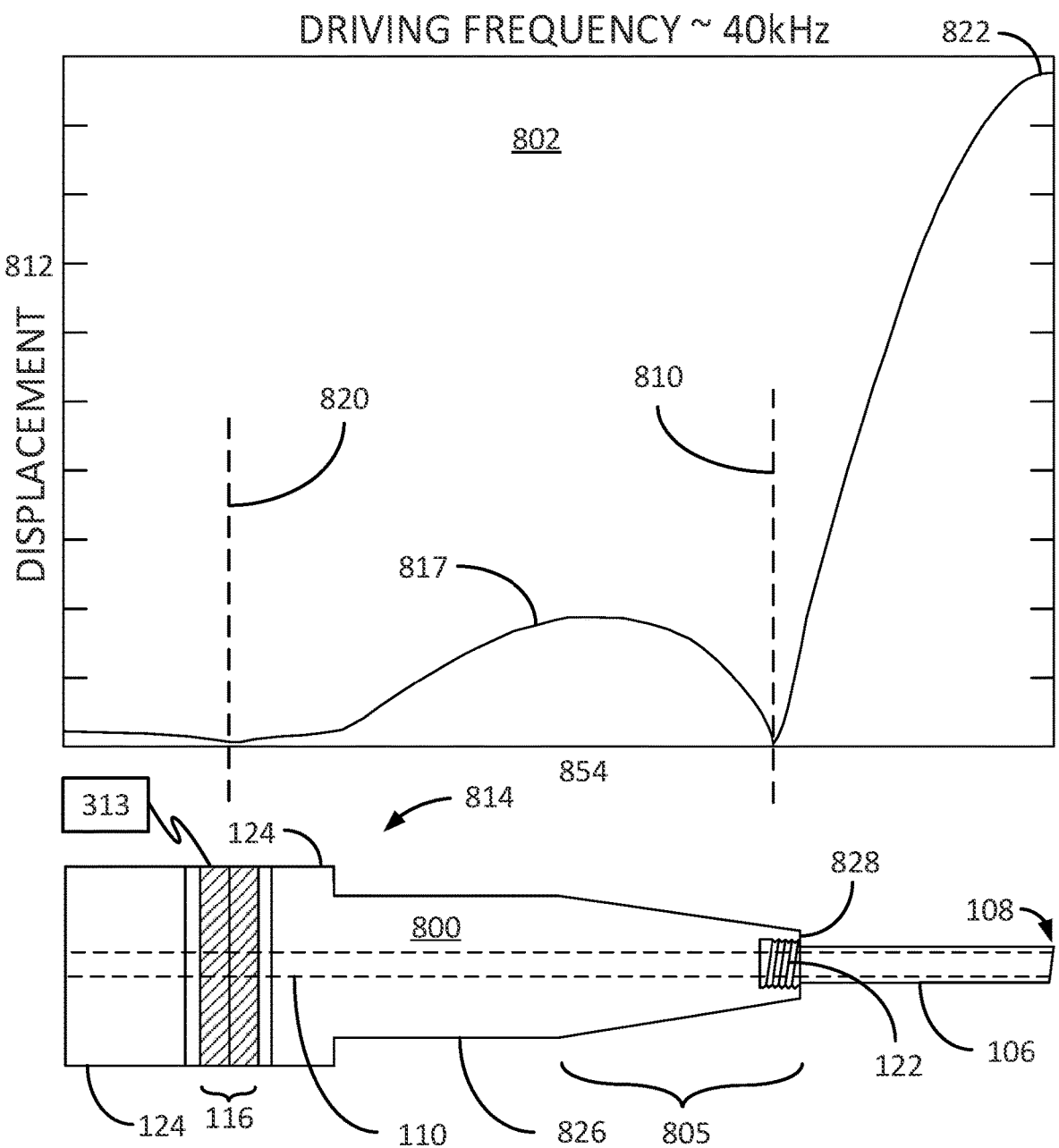
FIG. 8 is a line drawing of an ultrasonic frequency response plot with a driving frequency of approximately 40 kHz aligned with a handpiece embodiment consistent with embodiments of the present invention.
Figure 9:
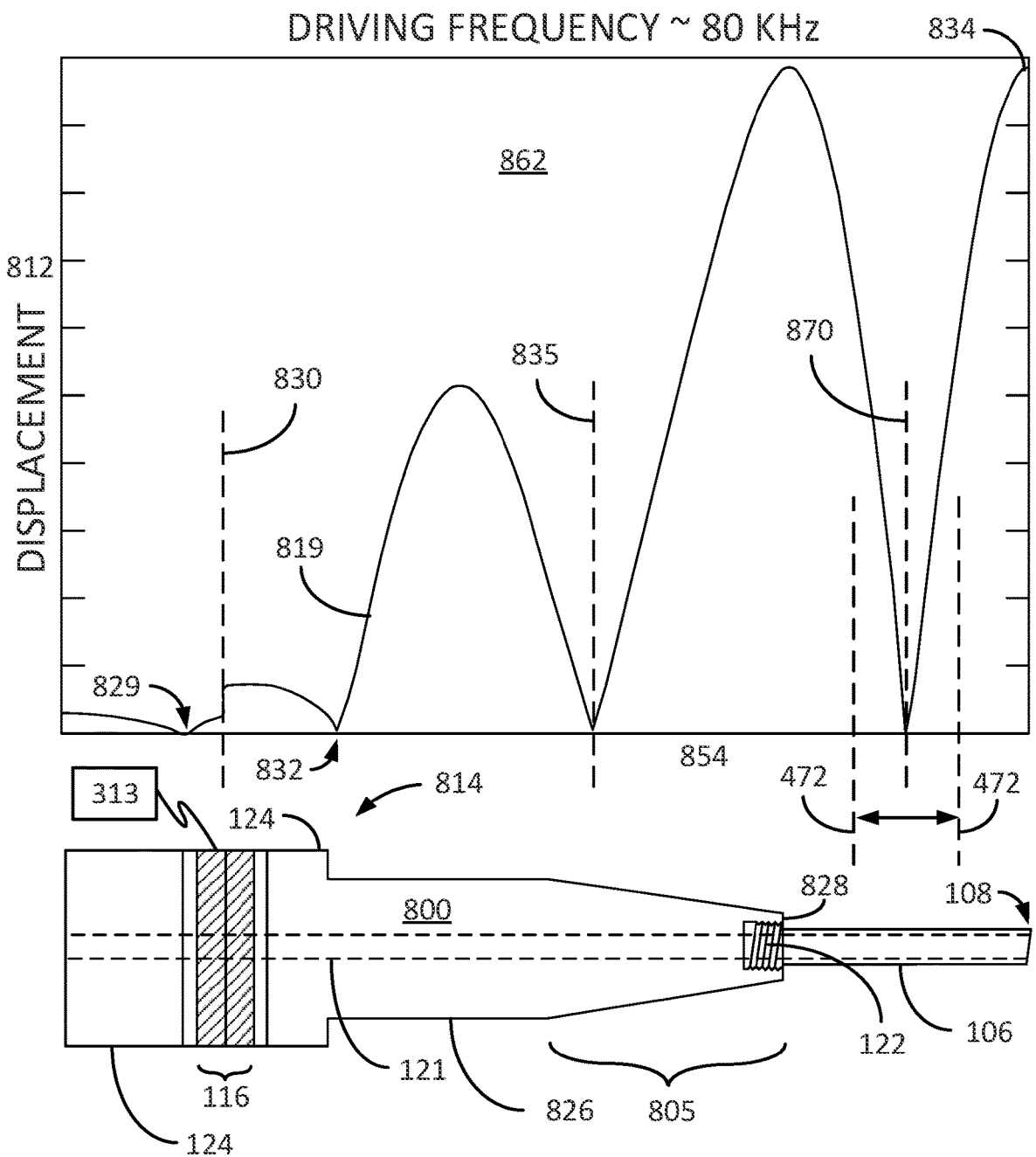
FIG. 9 is a line drawing of an ultrasonic frequency response plot with a driving frequency of approximately 80 kHz aligned with the handpiece embodiment of FIG. 8 consistent with embodiments of the present invention.

FIG. 8 illustratively depicts an optional embodiment of a handpiece with respect to a driving frequency of approximately 40 kHz consistent with embodiments of the present invention. An example of a driving frequency is an applied resonant frequency that excites the phacoemulsification device (or whatever element is being driven) subjected to the driving frequency causing the phacoemulsification device to resonate with a standing wave as shown in FIGS. 8 and 9. With respect to the present phacoemulsification device embodiment 800, the handpiece 814 includes a back cylinder 124 that comprises piezoelectric crystals 116 driven to vibrate by a control feedback circuit 313, which delivers an oscillating voltage to the piezoelectric transducer 116/124. In this embodiment, the back cylinder 124, which as depicted in FIG. 1 includes a rear portion 124A and a front portion 124B, includes two or more piezoelectric crystals 116 (e.g. ceramic discs) sandwiched between two metal cylinders, which can be made from titanium. The two or more piezoelectric crystals 116 can be compressed through a central bolt (not shown). Certain embodiments envision a Langevin transducer made up of four PZT8 piezo ceramics sandwiched between a stainless steel rod and a titanium rod. The two or more piezoelectric crystals 116 convert an applied voltage to longitudinally expand and contract. This is known as a "Langevin transducer". A step horn 826 is distal to the back cylinder 124 and the piezoelectric crystals 116. The step horn 826 comprises a tapered section 805 that tapers from a large diameter at a proximal end of step horn 826 to a small diameter at distal end 828 of step horn 826. Certain other embodiments envision the step horn 826 being a titanium cylinder with a smaller diameter than the Langevin transducer diameter. The aspiration passageway 110 extends through the handpiece 814 and the substantially cylindrical titanium needle (or just "needle") 106 exiting at a free distal tip 108. The needle 106 may or may not be cylindrical because in some cases, the substantially cylindrical titanium needle 106 may be tapered approximately five-thousandths of an inch from the supported end structure 122 to the free distal tip 108, which is near cylindrical or substantially cylindrical (in one example substantially means within +/−5% of being a perfect cylinder). The needle 106 screws into the step horn 826 distal end 828 via a supported end structure 122, which in this case are threads. A fastening hub (not shown) can further retained the needle 106 to the handpiece 814 at the distal end 828 of step horn 826. Certain embodiments contemplate the needle length being 0.7 inches long and the hub length being about 0.15 inches long with the needle OD being between 0.042 and 0.032 inches and an ID being between 0.027 and 0.020 inches, of some variation thereof.

The response plot is aligned with the phacoemulsification device embodiment 800 in that the length of the phacoemulsification device 800 spans of the length of abscissa 854 with a vibration response graph 802. The graph's y-axis 812 represents the displacement of the phacoemulsification device 800 and the x-axis 854 is the position/length along the phacoemulsification device 800. Hence, the amplitude response plot 817 is the vibrational displacement response of the low ultrasonic standing wave 817 along the length of the phacoemulsification device 800 at a driving frequency of approximately 40 kHz. As shown by the amplitude response 817, a handle node of minimum amplitude 820 is between the two piezoelectric crystals 116 that form the transducer 116/124. A second node of minimum amplitude (or tapered section node) 810 resides in the tapered section 805 of the step horn 826. At this low ultrasonic frequency, there is no node of minimum amplitude along the needle 106. Certain embodiments contemplate insuring that there is no node of minimum amplitude in the tapered segment 805 that is higher than ¼ of the low frequency wavelength, which in this case is around 40 kHz. For example, based on the physics of the system, the length of the tapered section 805 must be at least 0.6 inches with a wavelength of 4.8 inches (traversing the device 800) at a resonant frequency of 40 kHz. A distal antinode 822 at the free distal tip 108 causes a high displacement that is effective in fragmenting and emulsifying a cataractous lens of an eye 120. Certain embodiments envision a low driving frequency between 25 kHz and 45 kHz to provide both fragmentation and emulsification of cataractous lens material.

FIG. 9 illustratively depicts the handpiece of FIG. 8 with respect to a driving frequency of approximately 80 kHz consistent with embodiments of the present invention. As with FIG. 8, the length of the phacoemulsification device 800 spans or is otherwise aligned with the x-axis 854 along the vibration response graph 862. The vibration response graph 862 plots the amplitude standing wave response 819 of the phacoemulsification device 800 at a driving frequency of approximately 80 kHz. The amplitude standing wave response 819 is a high ultrasonic frequency standing wave. More specifically, the x-axis 854 corresponds with the position/length along the phacoemulsification device 800. Accordingly, the amplitude standing wave response 819 is the vibrational displacement response 812 along the length of the phacoemulsification device 800. As shown by the amplitude standing wave response 819, there are a number of different nodes of minimum amplitude at 80 kHz including a handle node 829, a handle-step horn/back handpiece interface node 832, a tapered section node 835, and a needle node 870. There is a high amplitude/displacement antinode 834 at or essentially at the free distal tip 108 (e.g., within 1.5 mm).

Some embodiments envision driving the frequency of the phacoemulsification device 800 between the low frequency of approximately 40 kHz and the high frequency of approximately 80 kHz to manage fragmentation and cavitation of cataractous lens material. As previously presented, fragmentation is the action of cutting or splitting the lens in fragments like a knife moving rapidly or otherwise very fast in a medium. In some cases, the ocular fragments 109 are sometimes too large to be sucked/aspirated through the aspiration passageway 110, let alone into the lumen/opening at the free distal tip 108. As discussed previously, this is a problem because a large fragment 590 (of FIG. 6) can occlude or otherwise block the aspiration passageway 110 at the free distal tip 108. Not only will a large fragment 590 block/obstruct the phacoemulsification device from aspirating ocular fragments 109 and providing irrigation fluid 111, heat can build up along the needle 106 potentially burning the eye incision/interface 101 (of FIG. 1). At lower frequencies, under 60 kHz and more typically between 25 and 45 kHz, cavitation of the liquid in the eye 120 at the free distal tip 108 serves to emulsify or otherwise disintegrate the fragmented cataractous lens material into small particles that are small enough to pass through the opening at the free distal tip 108 and into the aspiration passageway 110. Intense cavitation induced waves may push the lens fragments away from the free distal tip 108, which complicates maneuvering the free distal tip 108 in the eye 120. These ways can also have negative effects by dislocating healthy eye tissue. There have been reports of fragmented cataractous lens material being pushed/chased into the posterior portion of an eye 120. Higher frequencies, especially those equal to or above 60 kHz, generate less cavitation and above 100 kHz, cavitation almost disappears.

With this in mind, switching from a lower frequency under 60 kHz to a high frequency equal to or above 60 kHz has a number of benefits. For example, as shown in FIG. 9, at a high frequency the needle node of minimum amplitude 870 is considered a 'cold needle' because there is no ultrasonic vibration occurring at the node of minimum amplitude 870. The needle node of minimum amplitude 870 is in an eye interface region (where the needle 106 will mostly interface an eye incision 101 during surgery) along the needle 106 depicted by the double arrow between the boundary lines 472. Hence, if the needle 106 becomes occluded with a cataractous lens fragment at a low frequency, by switching to a high frequency the cataractous lens fragment can break up and be sucked through the aspiration passageway 110 more quickly avoiding overheating the needle 106 at the incision 101 if in the eye interface region between the boundary lines 472. Furthermore, the high frequency reduces cavitation generation, which as previously mentioned has its own problems. Some embodiments contemplate the high frequency and the low frequency both being purely longitudinal waves.

The tapered region 805 of the phacoemulsification device 800 can be lengthened, shortened, widened, etc., in order to better control the placement of a node of minimum amplitude along a needle 106 when vibrated at a high ultrasonic frequency. The geometry of the tapered region 805 further influences keeping a node of minimum amplitude from forming or otherwise existing along the needle 106. Certain other embodiments of the present invention do not limit the tapered region 805 from being conical but entertain additional shapes/profiles including elliptical, exponential, Gaussian, and Fourier, just to name a few. Certain commercial embodiments envision the total length of the handpiece 814 being approximately 3 inches long with a diameter of approximately 0.375 inches. The step horn 826 can be made of a titanium rod (matching the handpiece material) that is approximately 0.8 inches long and about 0.15 inches in diameter tapering conically down to 0.05 inches in diameter over a tapered region 805 that is approximately 1.2 inches long. The needle 106 can be approximately 0.8 inches long with an outside diameter of approximately 0.045 inches and an inside diameter of approximately 0.035 inches. The aspiration passageway 110 can be about 0.07 inches in diameter. A high frequency of equal to or above 60 kHz can be preferably, about 80 kHz in some embodiments, and a low frequency below 60 kHz, which in some embodiments is approximately 40 kHz. Other embodiments envision a low frequency below 50 kHz and a high frequency above 50 kHz. The phacoemulsification device 800 can be made to toggle between the low frequency and the high frequency automatically with the feedback system that may take into account one or more of the following: vacuum, flow rate, bottle height, procedure modes, or by way of an operator (surgeon command) toggling a foot switch, hand switch, or voice control, just to name a few examples. The software that controls the low frequency and high frequency can be executed via the computer controller 380 or equivalent computing device.

Figure 10:
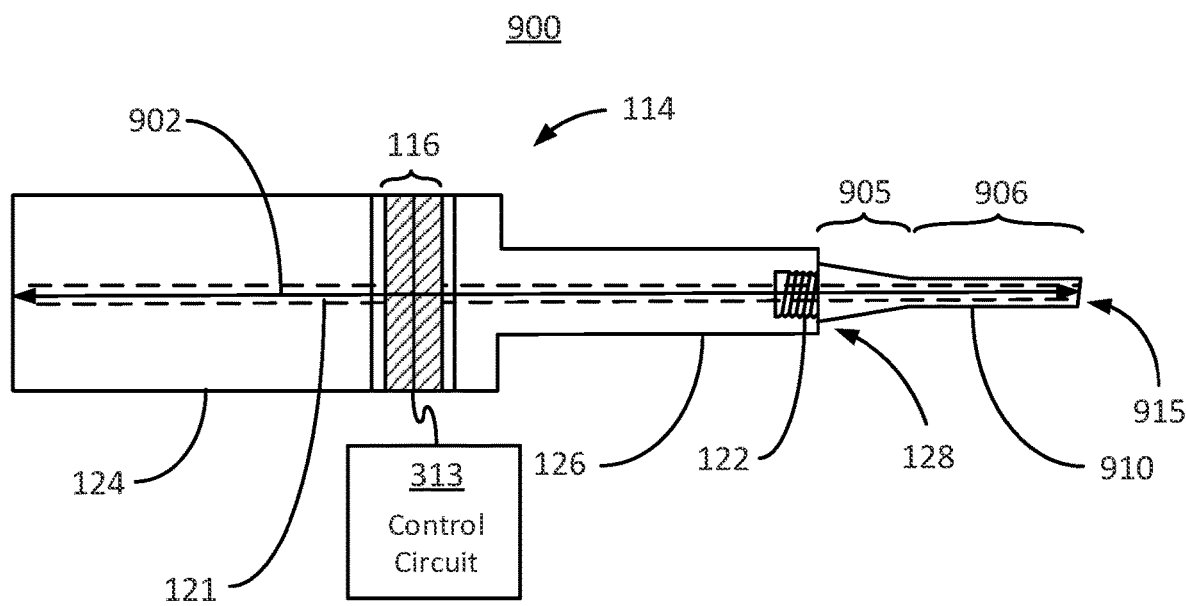
FIG. 10 is a line drawing of an optional phacoemulsification embodiment consistent with embodiments of the present invention.

FIG. 10 is a line drawing of yet another phacoemulsification embodiment consistent with embodiments of the present invention. As shown, the phacoemulsification handpiece 114 does not have a tapered region in the step horn 126. Rather, there is a tapered region 905 at the proximal end of the needle 910. In this embodiment, the tapered region 905 is configured to control the node of minimum amplitude along the substantially cylindrical portion 906 of the needle 910 when at a low ultrasonic frequency. As with the tapered portion 805 of the step horn 826 in the previous embodiment of FIGS. 8 and 9, a tapered node of minimum amplitude 810 can be designed to fall either within the tapered region 905 of the needle 910 or in the cylindrical step horn 126. Some embodiments envision the needle 910 being a unitary titanium element. For reference, a longitudinal axis 902 that extends from the back of the handpiece cylinder 124 to the free distal tip 915 is illustratively shown. The longitudinal axis 902 is a theoretical axis that can equally be applied to the other phacoemulsification devices, such as 800, described herein. During high ultrasonic frequencies, a node of minimum amplitude 870 can exist in the cylindrical portion 906, to create a 'cold needle' region at the cornea incision 101.

Figure 11A:
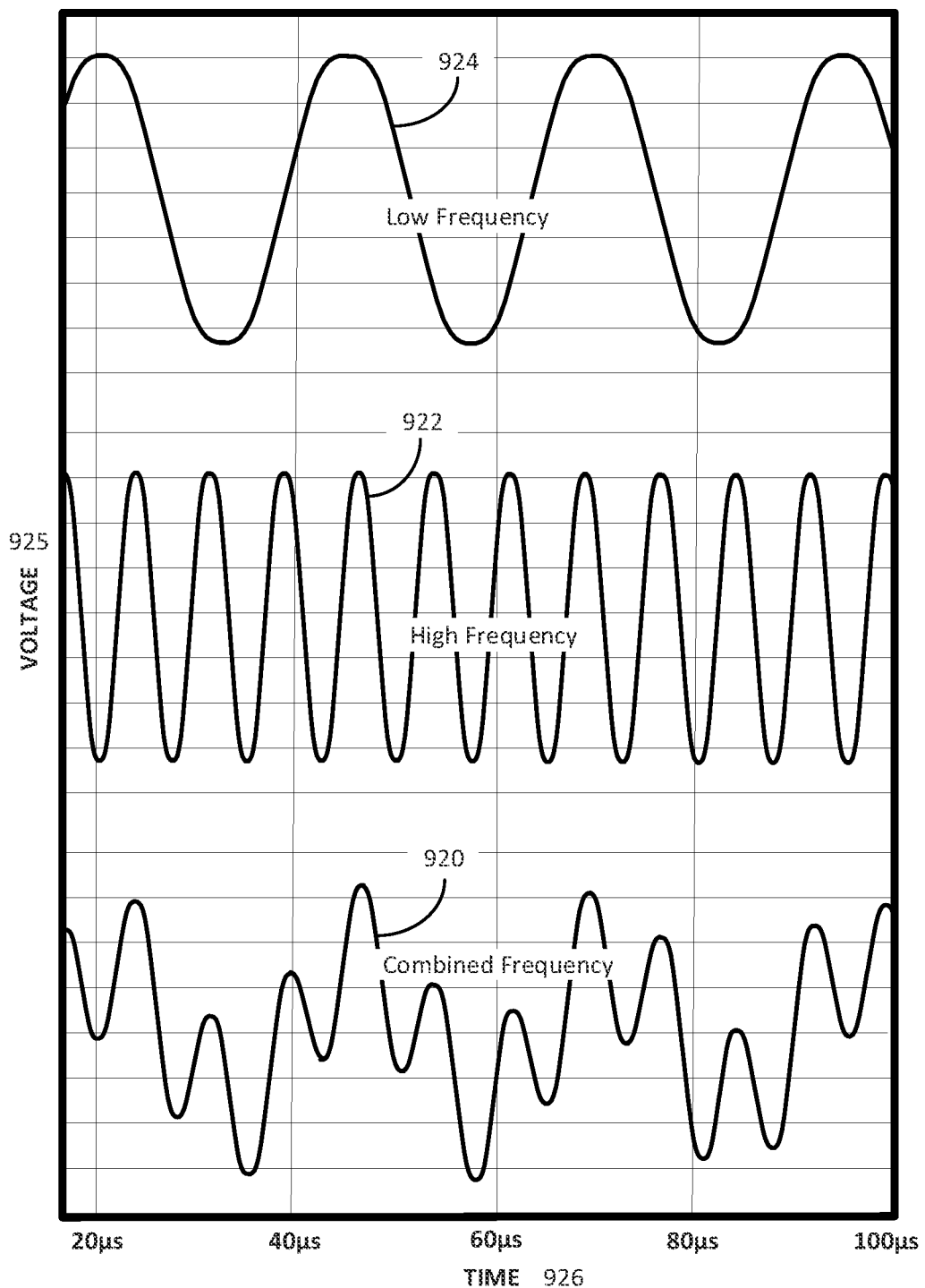
FIG. 11A graphically depict frequency plots of a low frequency response, a high frequency response and the superposition of the low and high frequency responses consistent with embodiments of the present invention.

FIG. 11A is an illustration of a low frequency plot superimposed on a high frequency plot consistent with embodiments of the present invention. More specifically, graphs of three frequency signals are plotted with voltage being in the y-axis (ordinate) 925 and time being in the x-axis 926 (abscissa) is shown. The low frequency signal 924 is added to the high frequency signal 922 to generate the combined frequency signal 920. As shown, the low frequency 924 and the high frequency 922 are each generated with essentially equal power, hence both the low frequency 924 and the high frequency 922 have about the same amplitude. In this way, the combined frequency 920 is not dominated by either the low frequency 924 or the high frequency 922. Certain embodiments envision the low frequency 924 having higher power than the high frequency 922 thereby generating a situation where the low frequency 924 is essentially a carrier frequency (not shown) of the high frequency 922. Likewise, if the high frequency 922 is generated via a higher applied power than the low frequency 924, the high frequency 922 will have a more dominating effect on the combined frequency (not shown). Certain embodiments of the present invention envision the piezoelectric transducer 116/124 of any phacoemulsification handpiece embodiment described herein generating the two frequencies 922 and 924, as shown in FIG. 11B.

Figure 11B:
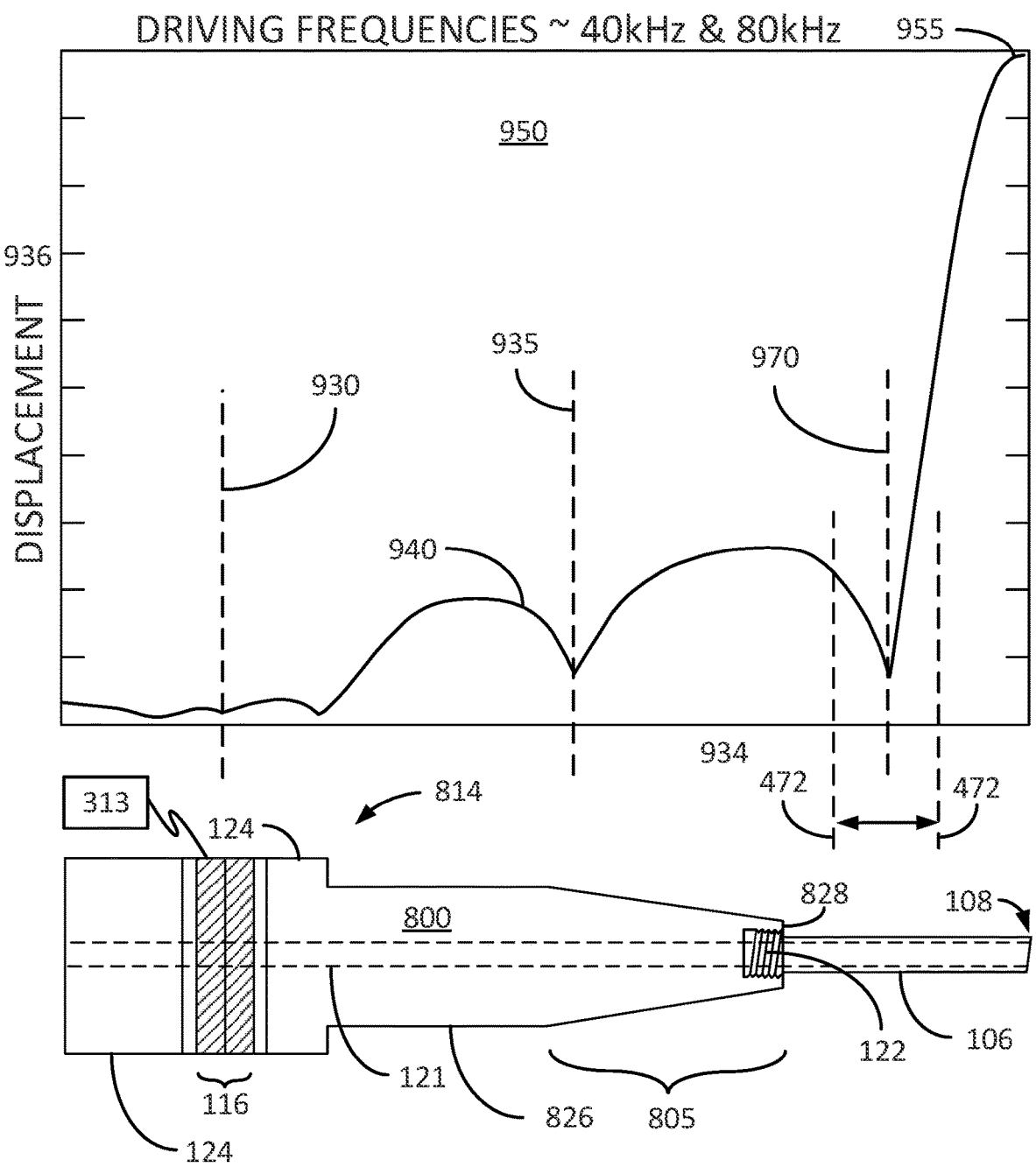
FIG. 11B is a line drawing of a combined high and low ultrasonic frequency response plot aligned with a handpiece embodiment consistent with embodiments of the present invention.

FIG. 11B is a plot of a standing wave at the combined frequencies with respect to a phacoemulsification device embodiment 800 consistent with embodiments of the present invention. As shown, the vibration response graph 950 is of a standing wave plot 940 of the combined two frequencies 922 and 924 resonating the phacoemulsification device 800. Here, the low frequency is approximately 40 kHz and the high frequency is approximately 80 kHz, however other certain embodiments envision the low frequency below 60 kHz and the high frequency being equal to or above 60 kHz. It is further envisioned that the standing wave plot 940 created by the high and low frequencies 922 and 924 is essentially a superposition of the high frequency standing wave 819 over the low frequency standing wave 817 (depicted in FIGS. 8 and 9). Accordingly, the displacement response plot 940 (i.e., the resonant displacement 936 of the phacoemulsification device 800 along the length 934 of the device 800) comprises a semi-node of low amplitude 935 in the tapered section 805 of step horn 826 and a single semi-node of low amplitude 970 along the length of the needle 106. Unlike the nodes of minimum amplitude 835 and 870 of FIG. 9, the semi-node of low amplitudes 935 and 970 do not have a near zero displacement of vibration on the device 800, rather they create a mere depression in the resonant response of the device 800. Accordingly, the needle 106 has a 'cool region' 472 instead of a 'cold region', depicted by the double arrow between the lines 472, The 'cool region' keeps the eye 120 from burning where the needle 106 interfaces the eye 120. As further shown, there is an antinode 955 approximately at the free distal tip 108 to enhance the cutting action and particle breakup.

Some embodiments of the present invention further envision a surgeon/operator adjusting power to the phacoemulsification device 800 to drive one of the frequencies to dominate over the other. More specifically, certain embodiments envision a switch, a foot pedal, voice control, or some other input, to simultaneously increase power of the high frequency mode 922 while proportionally decreasing power to the low frequency mode 924, and vise-versa. Increasing power to the high frequency mode 922 (with a proportional decrease in power to the low frequency mode 924) could be accomplished in discrete intervals or optionally smoothly over an infinite range of power levels, or somewhere in between. In this way, the needle 106 can be made to more effectively cut cataractous material into fragments while minimizing cavitation with a "cool" needle 106. Decreasing power to the high frequency mode 922 while proportionally increasing power to the low frequency mode 924 can serve to emulsify the fragments for better aspiration through the aspiration passageway 110. Having both frequencies used together provides certain benefits of more efficiently cutting and emulsifying fragments of cataractous eye material. When providing a surgeon with the opportunity to adjust the power of one frequency over another, maneuvering through a cataract surgery to remove cataracts can be accomplished more efficaciously. In short, in consideration that while lowering ultrasonic frequencies enhances cavitation but generates more heat, the higher frequencies increase fragmentation without increasing heat, the two frequencies can be combined in different proportions to best suit the situation. For example, driving the lower frequency with lower power and increasing power for the high frequency could help fragment harder cataract tissue when cutting is more important than most of the occasion. This can be done with purely longitudinal waves. By turning up or down the low frequency (and inversely proportionally forcing a down or up response to the high frequency), a surgeon will have improved control.

Though embodiments described in conjunction with FIG. 11B are directed to phacoemulsification device 800 with the tapered region 805, other embodiments of a phacoemulsification assembly 100 with no such taper can be employed as well. In other words, the aforementioned vibration concepts can be used in conjunction with any number of different phacoemulsification devices without departing from the scope and spirit of the present invention.

FIGS. 12-18 depict various piezoelectric transducer circuit embodiments arranged to drive a phacoemulsification needle at various frequencies consistent with embodiments of the present invention. Though any of the phacoemulsification device assemblies are combinable with at least the foregoing circuit diagrams described, the phacoemulsification assembly 100 of FIG. 3A is used in conjunction with the various circuit embodiments for purposes of explanation. As previously described, the piezoelectric transducer 116/124 includes two or more piezoelectric crystals 116 that are compressed or otherwise sandwiched between the rear back cylinder portion 124A and the front back cylinder portion 124B via a central bolt (not shown). In some embodiments, the rear back cylinder portion 124A, the front back cylinder portion 124B, the step horn 126 and the needle 106 are all made out of titanium. In certain embodiments, the piezoelectric crystals 116 are arranged in a Langevin transducer configuration that converts an applied cycled voltage to longitudinally expand and contract thereby driving vibrational resonance in the phacoemulsification assembly 100. The displacement at the front cylinder (step horn)/rear cylinder interface 125 is amplified compared to the displacement of the piezoelectric crystals 116. The step horn 126 further amplifies the vibration relative to the front cylinder/rear cylinder interface 125 because of the lower mass. Amplification of the step horn 126 is envisioned to be as much as 20 times greater at the distal end of the step horn 126 compared with the front cylinder/rear cylinder interface 125. Certain other embodiments envision changing the geometry/dimensions of the phacoemulsification device and/or materials used to alter or otherwise tailor the resonance. For example, a 4 inch long piezoelectric transducer 116/124 plus step horn 126 and a 0.7 inch long attached needle 106 may have a resonance frequency of about 40 kHz with higher resonances at 72 kHz, 82 kHz, 120 kHz, 152 kHz and so on. Some of these resonances generate motion at the needle tip and some do not.

Figure 12:
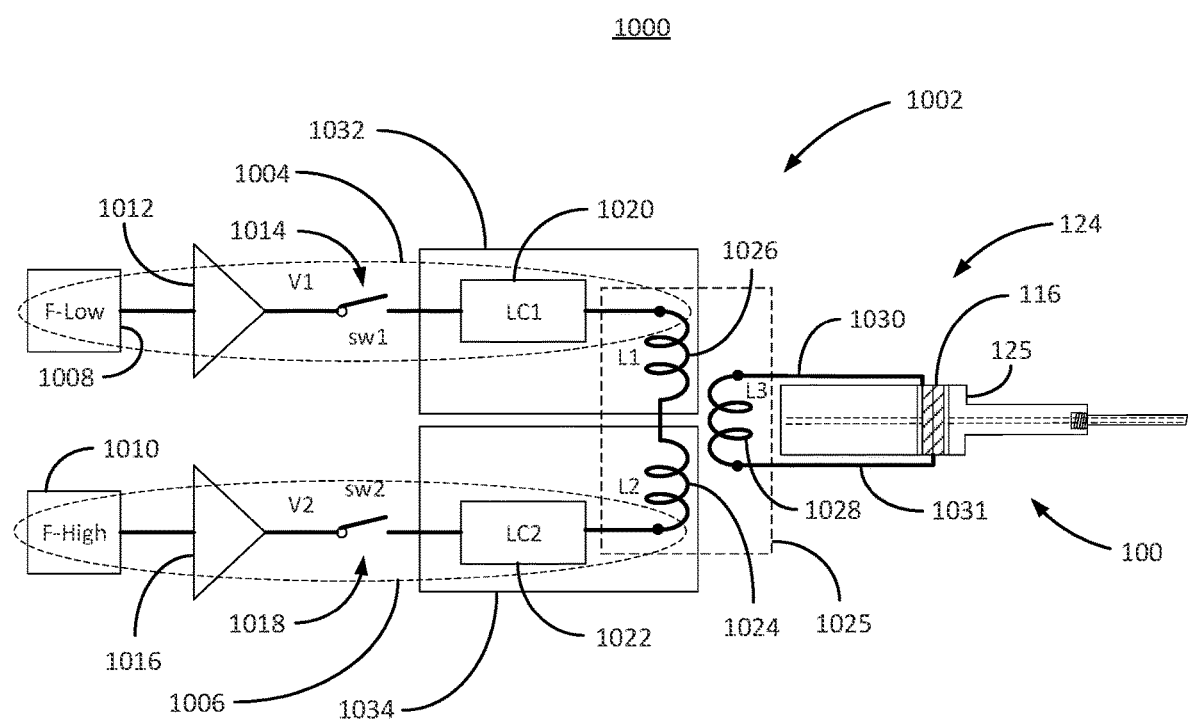
FIG. 12 is a line drawing of circuit layout embodiment for a dual frequency ultrasonic driver consistent with embodiments of the present invention.

FIG. 12 is a line drawing of circuit layout embodiment for a dual frequency ultrasonic driver consistent with embodiments of the present invention. As shown, the dual frequency ultrasonic diagram of a phacoemulsification arrangement 1000 depicts the phacoemulsification assembly 100 electrically connected to a dual frequency ultrasonic driver circuit 1002. When in operation, the ultrasonic driver circuit 1002 is envisioned to energize or otherwise drive the phacoemulsification assembly 100 with two different frequencies, a low-frequency and a high-frequency, applied either simultaneously or one at a time.

In this embodiment a low-frequency path 1004, as shown by the dashed oval 1004, generally includes a low-frequency oscillator 1008, a first voltage amplifier 1012, a first switch 1014 and a first impedance matching network 1032. When powered, the low-frequency oscillator 1008 generates a low frequency voltage signal, which in certain embodiments is under 60 kHz. The low frequency voltage signal can be in the form of a sine wave or a square wave, just to name a few of the many wave profiles known to those skilled in the art. The low-frequency voltage signal is amplified by a first power amplifier 1012 represented by an output voltage V1, which is then passed through a first impedance matching network 1032. In this configuration, the first impedance matching network 1032 comprises a first tapped transformer 1026 (depicted as inductor L1) electrically connected to a first LC filter 1020 (LC1) that filters the amplified low frequency signal generated by the low-frequency oscillator 1008. The LC1 filter 1020 can reduce noise, separate out or condition desired signals, for example. Typically, when capacitors or inductors are involved in an AC circuit, the current and voltage do not peak at the same time. When a voltage is applied to an inductor, the inductor resists the change in current. The current builds up more slowly than the voltage, lagging it in time and phase. On the other hand, since the voltage applied to a capacitor is directly proportional to the charge on the capacitor, the current must lead the voltage in time and phase to conduct charge to the capacitor plate and raise the voltage. The fraction of a period difference between the peaks expressed in degrees is considered the phase difference. The phase difference is obviously less than or equal to 90 degrees. Those skilled in the art generally use the angle by which the voltage leads the current, which results n a positive phase for inductive circuits since current lags the voltage in an inductive circuit. The phase Is negative for capacitive circuit since current leads the voltage. Hence, in order to deliver the alternating current and voltage efficiently to the piezoelectric transducer 116/124, certain embodiments of the present invention envision balancing the LC1 circuit 1020 to output essentially an in-phase alternating voltage and current. Certain other embodiments envision the phase difference between the voltage and current being within +/−10%. Likewise, the high-frequency path 1006, as shown by the dashed oval 1006, includes a high-frequency oscillator 1010, a second voltage amplifier 1016, a second switch 1018 and a second impedance matching network 1034. When powered, the high-frequency oscillator 1010 that generates a high frequency voltage signal, which certain embodiments is equal to or above 60 kHz. The high-frequency voltage signal is amplified by a second power amplifier 1016 represented by an output V2, which is then passed through a second impedance matching network 1034. The second impedance matching network 1034 comprises a second tapped transformer 1024 (depicted as an inductor L2) electrically connected to a second LC filter 1022 (LC2). For single frequency operation, the secondary winding of a tapped transformer multiplies the voltages V1 and V2 by the transformer turn ratio and the resonance matching effect of the impedance matching network 1032/1034. Some embodiments envision the power amplifiers 1012 and 1016 each being a class AB amplifier, a half bridge class C amplifier or a full bridge class D amplifier.

The switches, SW1 1014 and SW2 1018, connect the low-frequency path 1004 and/or the high-frequency path 1006 to facilitate single or simultaneous frequency operation. For example, when the first switch 1014 (SW1) is closed, the low-frequency path 1004 actively drives the piezoelectric transducer 116/124 to vibrate at the low-frequency by way of transforming energy through third tapped transformer 1028 (depicted as an inductor L3) that is in the piezoelectric transducer connecting circuit leg 1030. L1 1026, L2 1024 and the third tapped transformer 1028 (depicted as an inductor L3) generally make up the inductive transformer 1025 that supplies power to the two wires 1030 and 1031 used for connecting the dual frequency driver circuit 1002 through the piezoelectric crystals 116. When the second switch 1018 (SW2) is closed, the high-frequency path 1006 actively drives the piezoelectric transducer 116/124 to vibrate at the high-frequency by way of transforming energy through L3 1028. If both the first switch 1014 (SW1) and the second switch 1018 (SW2) are closed, the piezoelectric crystals 116 can make the phacoemulsification assembly 100 vibrate at a combined frequency, like the combined frequency 920 depicted in FIG. 11A. For single frequency operation the secondary winding of a tapped transformer multiplies the voltages V1 and V2 by the transformer turn ratio and the resonance effect of the matching network. For simultaneous frequency operation, the sum of V1 and V2 is multiplied. In this example, the secondary winding L3 1028 is connected to the piezoelectric crystals 116. Only two wires are used for connecting the driver circuit 1002 to the piezoelectric transducer 116/124. The inductive transformer 1025 can further function as a frequency mixer that changes the percent contribution of the output low voltage and low current relative to and inversely proportional to the output high voltage and high current. For example, if the inductive transformer 1025 changes the output low voltage and low current to 25%, the output high voltage and high current is 75% of the total combined (superimposed) output voltage and current. An example of a combined output voltage is graphically depicted in FIG. 11A. Another mixer embodiment is by way of proportionally changing the amplification of the respective high and low signals output via the amplifiers 1012 and 1016, just to name another example of many. This can be accomplished by an actuator (not shown) controlled either manually (i.e., a foot pedal, knob, button, voice control, etc.) or via a computer system.

Figure 13A:
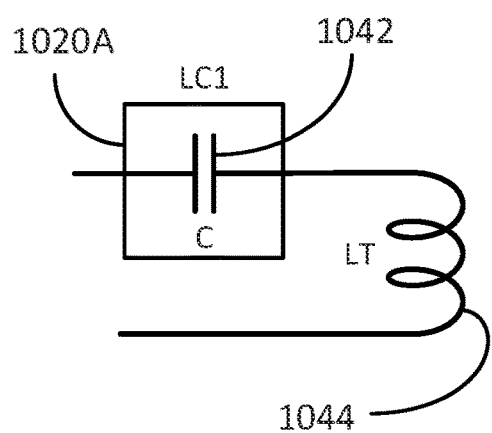
FIGS. 13A-13C are line drawings of various LC network block diagrams using a tapped transformer with a primary LT winding consistent with embodiments of the present invention.
Figure 13B:
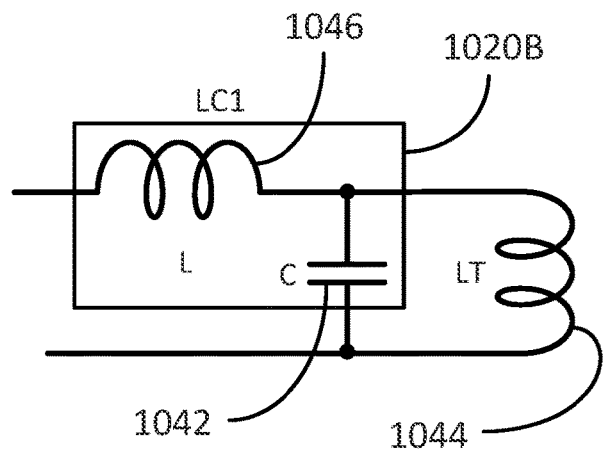
Figure 13C:
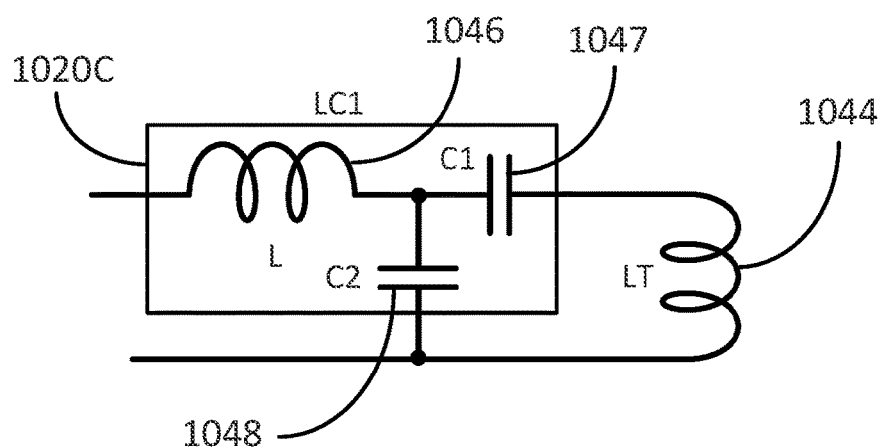

FIGS. 13A-13C are line drawings of various LC network block diagrams using a tapped transformer with a primary LT winding consistent with embodiments of the present invention. Each of the LC networks 1020 and 1022 generally comprise an inductor and capacitor configuration that connects to a primary LT winding, which in the embodiment of FIG. 12, the primary LT winding is L1 1026 and L2 1024. These LC (inductor and capacitor) networks can assume a number of different configurations, with three depicted examples. LC filter network LC1 1020A of FIG. 13A is a simple capacitor 1042 (C) connected to the LT winding 1044, which in FIG. 12 is either L1 1026 or L2 1024, however some embodiments it could be L1 1026 and L2 1024. FIG. 13B is LC filter network LC1 1020B comprising an inductor 1046 (L) and capacitor 1042 (C) connected to the LT winding 1044. FIG. 13C is LC filter network LC1 1020C comprising inductor 1046 (L) and two capacitors (C1 1047 and C2 1048) connected to the LT winding 1044. Certain embodiments contemplate that the impedance matching network 1020A, B or C comprise an LC network (LC1 1020 and LC2 1022 of FIG. 12) and the primary winding of a tapped transformer (L1 1026 and L2 1024, also of FIG. 12). Different LC networks inductor/capacitance configurations can be used without departing from the scope and spirit of the present invention.

Figure 14:
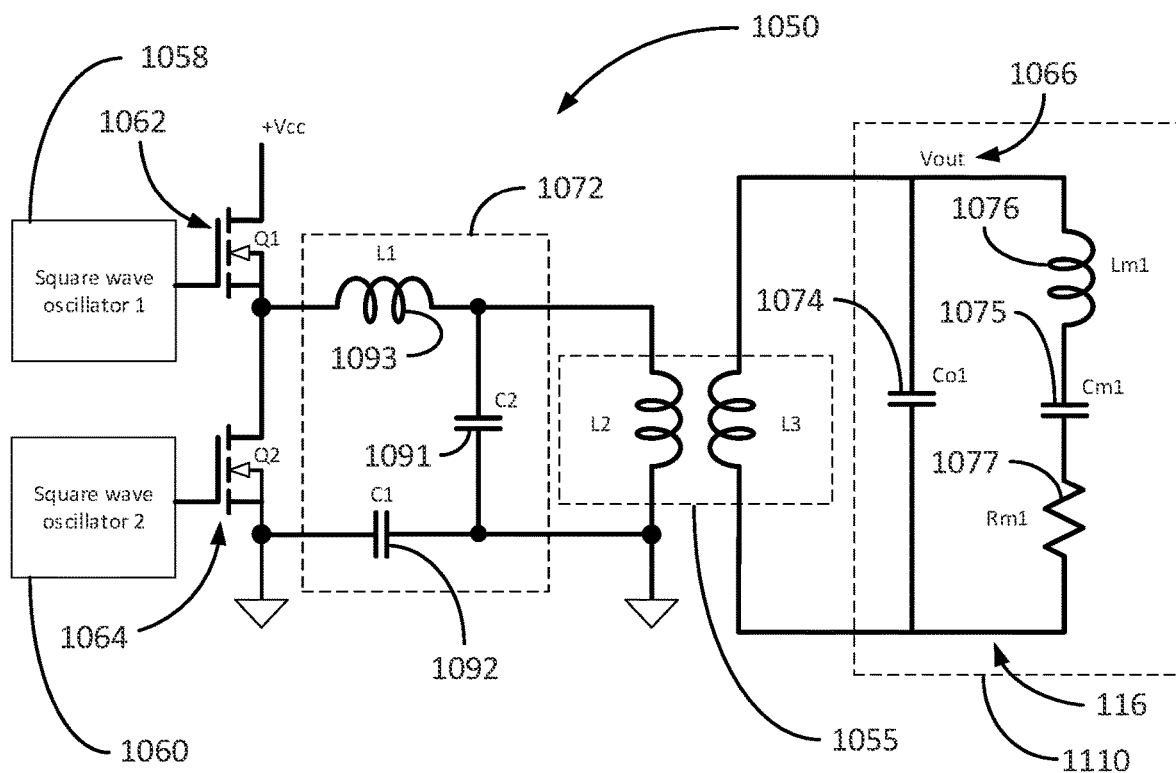
FIG. 14 is a line drawing of circuit layout embodiment fora half bridge class C ultrasonic driver circuit for a piezoelectric transducer consistent with embodiments of the present invention.

FIG. 14 is a line drawing of circuit layout embodiment for a half bridge class C ultrasonic driver circuit for a piezoelectric transducer consistent with embodiments of the present invention. As shown, the half bridge class C ultrasonic driver circuit 1050 connects to the piezoelectric transducer 116/124 by way of the inductive transformer 1055. Square wave oscillator-1 1058 must run out of phase with square wave oscillator-2 1060 such that only the corresponding transistor Q1 1062 or Q2 1064 is turned ON at a given time. In other words, when square wave oscillator-1 1058 produces a 'high' square wave signal amplitude, transistor Q1 1062 is turned ON while transistor Q2 1064 is turned OFF. In this scenario, square wave oscillator-2 1060 produces a 'low' square wave signal amplitude while square wave oscillator-1 1058 is producing a 'high' square wave signal amplitude. Of course, the opposite scenario can equally occur wherein transistor Q1 1062 is turned OFF when square wave oscillator-1 1058 produces a 'high' square wave signal amplitude and transistor Q2 1064 is turned ON while square wave oscillator-2 1060 produces a "low" square wave signal amplitude.

The two transistors Q1 1062 and Q2 1064 amplify the low voltage pulses produced by the square wave oscillators 1058 and 1060 into a high-voltage square wave Vcc. Because the piezoelectric transducer has a high quality factor, if the frequency of the two square wave oscillators 1058 and 1060 match the resonant frequency of the phacoemulsification assembly 100 then the high-voltage square wave Vcc is converted to a near perfect sine wave. Certain embodiments envision the output voltage 1066 (Vout) driving the piezoelectric transducer 116/124 with a voltage of about 700 V peak-to-peak. The impedance matching network 1072, which includes L1 1093, C1 1092, C2 1091, and the inductive transformer 1055 are electrically matched with the natural frequency of the piezoelectric transducer 116/124 (handpiece 114 and possibly the needle 106 as well). This can be modeled to include equivalent (imaginary) electrical elements, which in this example includes capacitors Co1 1074, Cm1 1075, inductor Lm1 1076 and resistor Rm1 1077, shown in phacoemulsification assembly dashed box 1110. At the physical resonant frequency or frequencies of the phacoemulsification assembly 100 (represented by the electrical elements in the phacoemulsification assembly dashed box 1110), Lm1 1076 and Cm1 1075 cancel out. This is referred to as series resonance. In one example, when the phacoemulsification assembly 100 has a natural frequency that resonates at 39.68 kHz, and there is series resonance, there is no phase offset between the output voltage Vout and the output current when the input signal pulses from the square wave oscillators 1058 and 1060 are also 39.68 kHz. For example, by matching the impedance of the power amplifiers 1062 and 1064 with the impedance of the phacoemulsification assembly 100 and running the square wave oscillators 1058 and 1060 at the resonant frequency of 39.68 kHz, a Vcc of 100 Vdc is converted to about a 700 V sine wave necessary to drive/vibrate the phacoemulsification assembly 100. This will generate a near maximum transfer of power, which in this case is about 25 W. When calculating the matching network components, the circuit of FIG. 15 can be used to determine the resonant frequency of between +/−10%.

Figure 15:
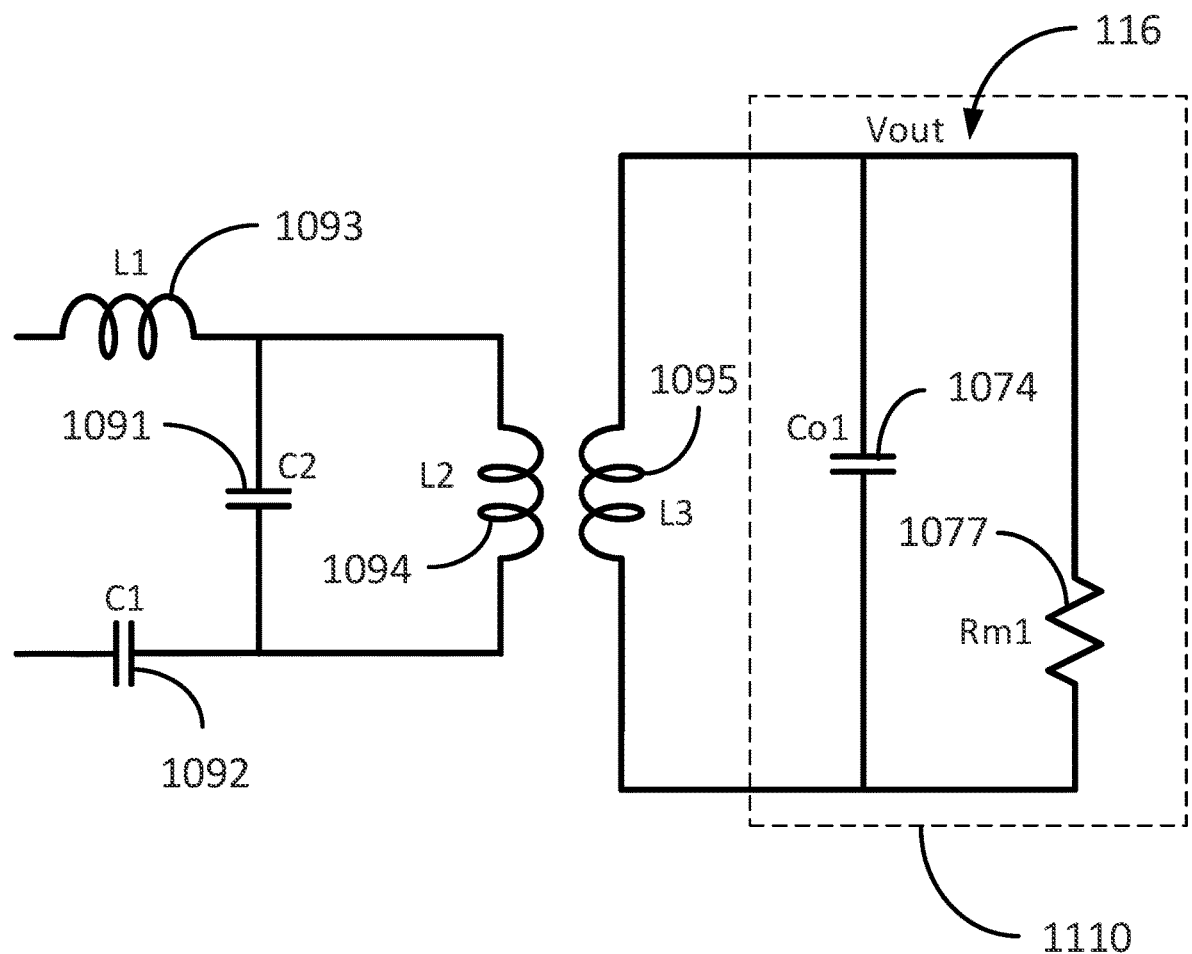
FIG. 15 is an example of a circuit layout embodiment for modeling the half bridge class C ultrasonic driver circuit of FIG. 14 consistent with embodiments of the present invention.

FIG. 15 is an example of a circuit layout embodiment for modeling the half bridge class C ultrasonic driver circuit of FIG. 14 consistent with embodiments of the present invention. The matching impedance components and test configuration of FIG. 15 assumes that capacitor Co1 1074 and resistor resister Rm1 1077 are the same as the inherent components of the phacoemulsification assembly 100, represented by the phacoemulsification assembly dashed box 1110. Capacitor Co1 1074 corresponds with the capacitance of the piezoelectric crystals 116 plus the capacitance of the handpiece 114 measured at the operating frequency. Resistor Rm1 1077 is the electrical equivalence of the resistive part of the phacoemulsification assembly load plus the mechanical losses. These components (capacitor Co1 1074 and resistor resister Rm1 1077) can be measured using an impedance analyzer. Values from the components, inductors L1 1093, L2 1094, L3 1095, and capacitors C1 1092 and C2 1091, are calculated as a function of capacitor Co1 1074 and resistor Rm1 1077.

Figure 16:
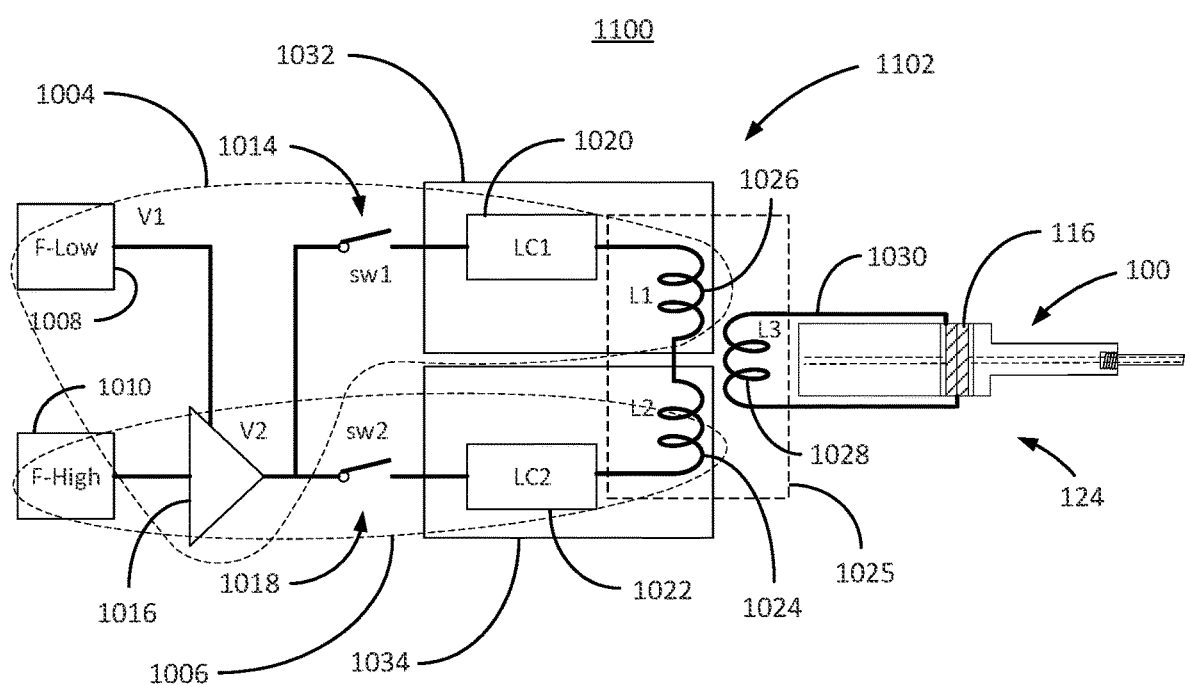
FIG. 16 is a line drawing circuit diagram of yet another driving circuit embodiment consistent with embodiments of the present invention.

FIG. 16 is a line drawing circuit diagram of yet another driving circuit embodiment consistent with embodiments of the present invention. In this optional dual frequency driver embodiment 1100, the ultrasonic frequency circuit configuration 1102 only uses one amplifier 1016 to amplify both the low-frequency oscillator 1008 and the high-frequency oscillator 1010. In this example, the low-frequency oscillator 1008 and the high frequency oscillator 1010 generate a sinusoidal waveform that energizes the piezoelectric transducer 116/124 via the inductive transformer 1025. As shown, the low-frequency path 1004 incorporates the common amplifier 1016 as does the high-frequency path 1006. The amplifier 1016 is a class AB amplifier. The components that comprise the LC networks 1020 and 1022 included in the impedance matching network may create one or more resonances different from the resonant frequencies of the phacoemulsification assembly 100 that includes the piezoelectric transducer 116/124. As previously discussed, if the impedance network 1102 is closely matched with the output frequency of the phacoemulsification assembly 100, the phacoemulsification assembly 100 will resonate at its natural frequency. By matching the natural frequency of at least the handpiece 114, and possibly the needle 106, with the electrical output frequency of the circuit 1102, the system is more efficient. Certain embodiments envision matching the natural frequency of only the handpiece 114 with the circuit 1002 because the handpiece 114 (and not the needle 106) overwhelmingly dictates the natural frequency. In other words, the mass and therefore the frequency response of the handpiece 114 contributes to the majority of the phacoemulsification assembly 100. Matching the electrical circuit 1002 with the natural frequency of the handpiece 114 (and possibly the needle 106 too) avoids excessive heat generation, buzzing, and other losses. In practice, it may be acceptable to match these frequencies within +/−10% to the frequencies generated by the oscillators 1008 and 1010.

Figure 17:
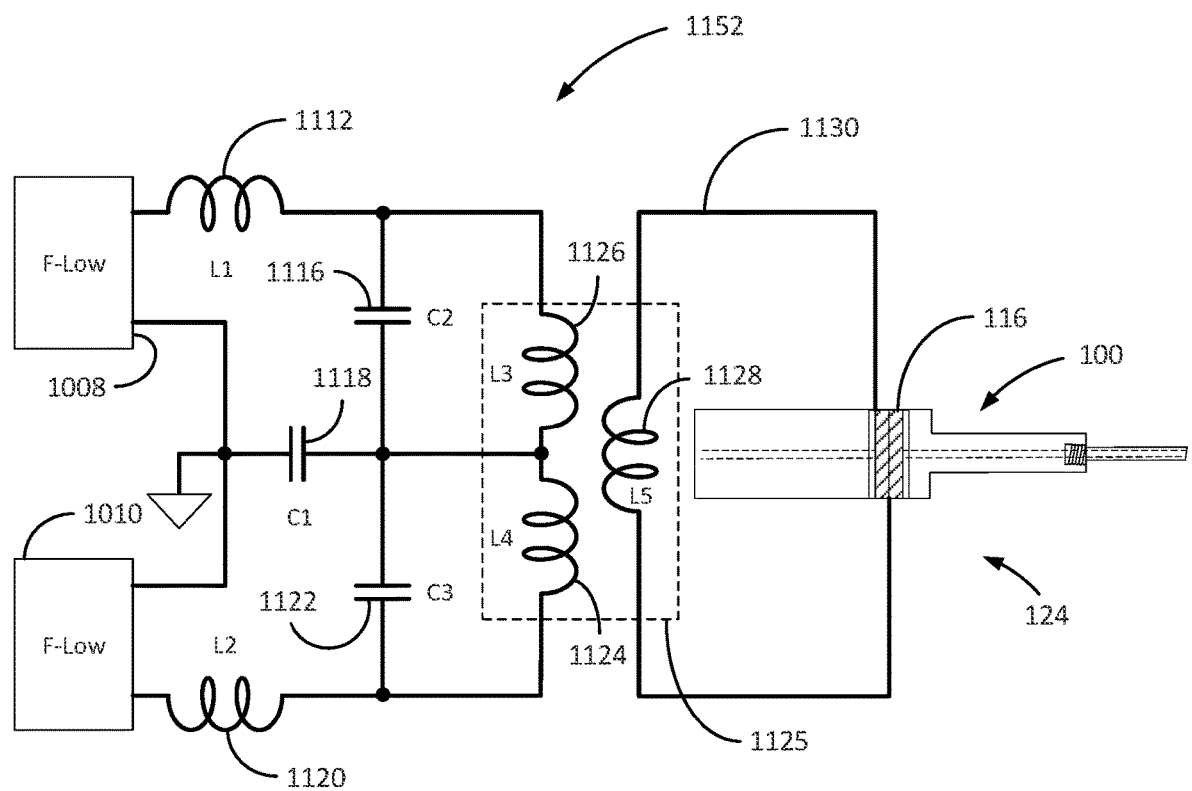
FIG. 17 is a line drawing circuit diagram of multiple oscillators producing different system matched frequencies consistent with embodiments of the present invention.

FIG. 17 is a line drawing circuit diagram of multiple oscillators producing different system matched frequencies consistent with embodiments of the present invention. FIG. 17 is an example of a dual frequency ultrasonic system 1150 powered by the ultrasonic driver circuit 1152. In this ultrasonic driver circuit embodiment 1152, a low-frequency oscillator 1008 and a high frequency oscillator 1010 generate respective frequency signals that can be applied to the phacoemulsification assembly 100 simultaneously or successively (i.e., one at a time). As shown, the low-frequency oscillator 1008 feeds into the upper LC circuit of L1 1112 and C2 1116 and the high-frequency oscillator 1010 feeds into the lower LC circuit of L2 1120 and C3 1122. The upper LC circuit and the lower LC circuit share a common capacitor C1 1118. The oscillating voltage is transferred from the ultrasonic driver circuit 1152 to the piezoelectric transducer 116/124 via the inductive transformer 1125, which comprises inductor L3 1126, inductor L4 1124 and inductor L5 1128.

Here, the network for the low ultrasonic electrical frequency (F-low) is matched with a low physical natural frequency of the phacoemulsification assembly 100 and the high ultrasonic electrical frequency (F-high) is likewise matched with a higher physical natural frequency of the phacoemulsification assembly 100. Hence, in this dual frequency driver embodiment 1150, the resonant frequencies of the impedance matching networks for the high and low ultrasonic frequency circuit configuration 1152 closely match the natural frequencies of the phacoemulsification assembly 100. Certain practical embodiments envision matching these frequencies within +/−10% being acceptable. Though not shown, a feedback system is envisioned to determine F-low and F-high (and the contribution of impedance matching network frequency responses) by reading the natural frequencies of the phacoemulsification assembly 100 and matching F-low and F-high against those natural frequencies to increase a resonance response.

Figure 18:
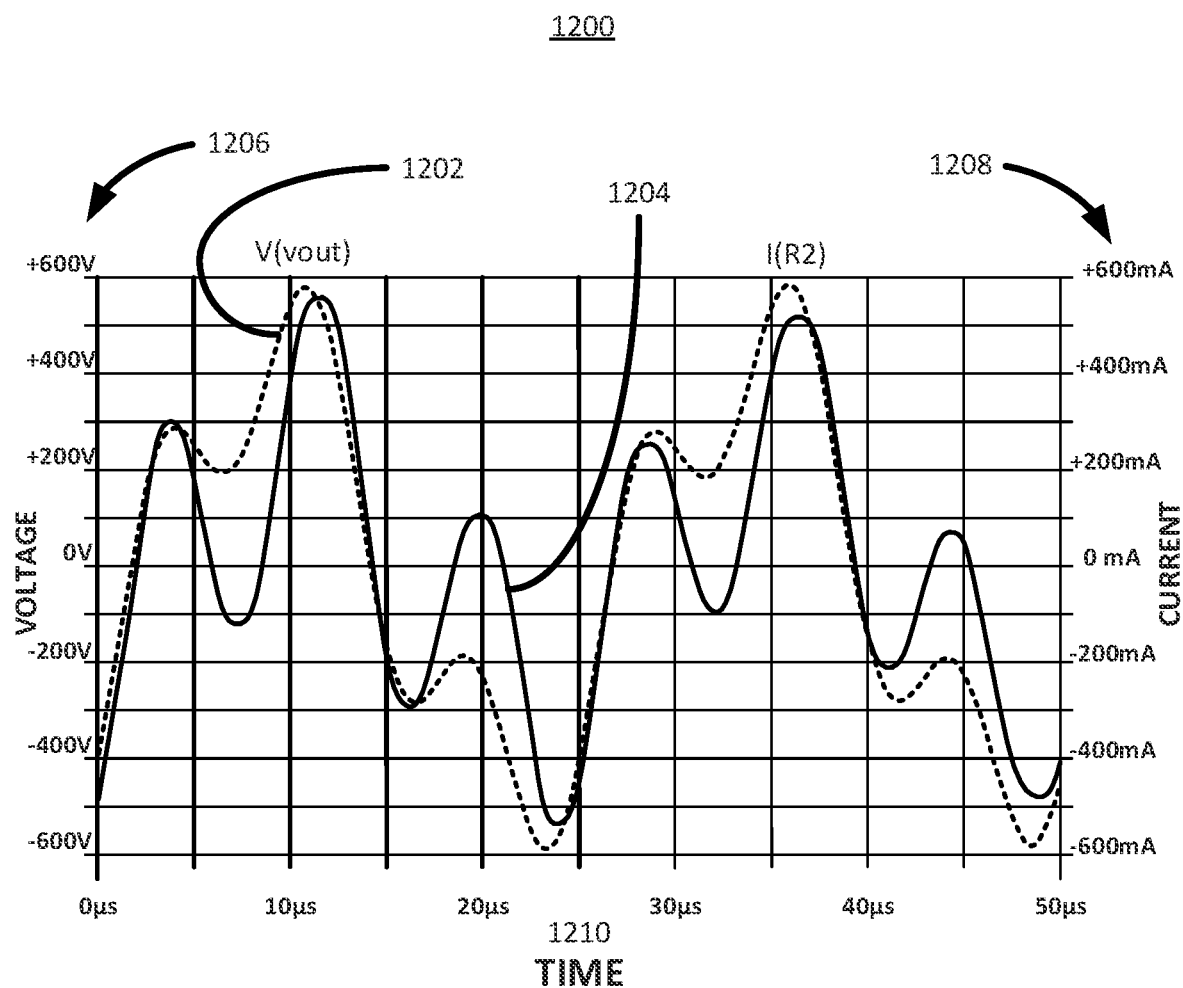
FIG. 18 illustratively depicts a line drawing of a current/voltage graph displaying a voltage plot essentially in-phase with a current plot consistent with embodiments of the present invention.

Another aspect of a balanced system is providing an in-phase current and voltage that are produced along both the low-frequency path 1004 and the high-frequency path 1006. FIG. 18 illustratively depicts a current/voltage graph 1200 displaying a voltage plot 1204 essentially in-phase with a current plot 1202. Both the voltage plot 1204 and the current plot 1202 are of a combined high and low frequency, exemplified in the voltage plot 920 of FIG. 11A. As shown, though the voltage plot 1204 has a different amplitude than the current plot 1202, the two plots 1204 and 1202 are essentially in-phase. For reference, the current/voltage graph 1200 present voltage 1206 and current 1208 in the y-axis versus time 1210 in the x-axis. Voltage values 1206 are displayed along the left y-axis and current values 1208 are displayed along the right y-axis. Because in reality no two systems are alike and perfectly aligning the phases of current and voltage is impractical in production, certain embodiments envision essentially in-phase to mean within less than +/−10% having the same phase. Because the circuit elements described herein generally relate to LC networks, such as LC1 1020 and LC2 1022 of FIG. 12, LC networks are preferably balanced to maintain in-phase current and voltage. Out of phase current and voltage generally leads to losses in the system, such as a buildup of heat instead of a clean transfer of signal, for example. Typically, when capacitors or inductors are involved in an AC circuit, the current and voltage do not peak at the same time. When a voltage is applied to an inductor, the inductor resists the change in current. The current builds up more slowly than the voltage, lagging it in e and phase. On the other hand, since the voltage applied to a capacitor is directly proportional to the charge on the capacitor, the current must lead the voltage in time and phase to conduct charge to the capacitor plate and raise the voltage. The fraction of a period difference between the peaks expressed in degrees is considered the phase difference. The phase difference is obviously less than or equal to 90 degrees. Those skilled in the art generally use the angle by which the voltage leads the current, which results in a positive phase for inductive circuits since current lags the voltage in an inductive circuit. The phase is negative for a capacitive circuit since current leads the voltage. Hence, in order to deliver the alternating current and voltage efficiently to the piezoelectric transducer 116/124, certain embodiments of the present invention envision balancing the LC1 circuit 1020 to output essentially an in-phase alternating voltage and current.

With the present description in mind, below are some examples of certain embodiments illustratively complementing some of the methods and apparatus embodiments to aid the reader. The elements called out below are examples provided to assist in the understanding of the present invention and should not be considered limiting.

In that light, certain embodiment contemplate a phacoemulsification arrangement 1000 as shown in FIG. 12 comprising a needle 106 extending from a handpiece 114 that includes a piezoelectric crystals 116 connected to a dual frequency producing circuit 1002 comprising a low-frequency oscillator 1008 and a high-frequency oscillator 1010. The dual frequency producing circuit 1002 electrically connected to the piezoelectric crystals 116 by way a wires 1030 and 1031. The low-frequency oscillator 1008 is configured to drive the piezoelectric transducer 116/124 to periodically vibrate the needle 106 at a low frequency defined as being less than 60 kHz without producing a node of minimum amplitude along the needle 106. The high-frequency oscillator 1010 is configured to drive the piezoelectric crystals 116 to periodically vibrate the needle 106 at a high frequency of more than 60 kHz while producing a single node of minimum amplitude 870 along the needle 106.

The phacoemulsification arrangement 1000 further envisioning wherein the dual frequency producing circuit is external to the needle 106 and the handpiece 114.

The phacoemulsification arrangement 1000 further pondering wherein the low-frequency oscillator 1008 is operable with the high-frequency oscillator 1010 to collectively periodically vibrate the needle 106 with a standing wave 940 that is defined by the low frequency standing wave 817 superimposed over the high frequency standing wave 819. This embodiment can further comprise an actuator that changes a percent contribution of the low-frequency standing wave 817 inversely proportional to the high-frequency standing wave 819 when generating the standing wave 940. Optionally, this embodiment can further be wherein the standing wave 940 comprises a single node of reduced amplitude 970 along the needle 106, the single node of reduced amplitude 970 is a higher amplitude than the single node of minimum amplitude.

The phacoemulsification arrangement 1000 further imagining wherein the dual frequency producing circuit 1002 comprises a low-frequency pathway and a high-frequency pathway, the low-frequency pathway comprising a low-frequency LC network 1032 tied to the low-frequency oscillator 1008 and the high-frequency pathway comprising a high-frequency LC network 1034 tied to the high-frequency oscillator 1010. Here, a tapped output transformer 1028 is inductively coupled to the low-frequency LC network 1032 and the high-frequency LC network 1034. The tapped output transformer 1028 is electrically connected to the piezoelectric crystal transducer 116. The tapped output transformer 1028 is configured to drive the piezoelectric crystals 116 with a low-frequency voltage from the low-frequency LC network 1032 and a high-frequency voltage from the high-frequency LC network 1034, or combination of the high frequency voltage and the low-frequency voltage. This embodiment can further comprise a low-frequency circuit resonance corresponding to the low-frequency LC network 1032 and a high-frequency circuit resonance corresponding to the high-frequency LC network 1034, the low frequency circuit resonance matching a first natural frequency of the needle 106 and the handpiece 114, the high-frequency circuit resonance matching a second natural frequency of the 106 and the handpiece 114.

The phacoemulsification arrangement 1000 further considering an embodiment wherein the needle 106 and the handpiece 114 are only applicable to cataract surgery using the phacoemulsification procedure.

The phacoemulsification arrangement 1000 further contemplating wherein the dual frequency producing circuit 1002 further comprising a low-frequency LC network 1032 corresponding to and connected to the low-frequency oscillator 1008 and the high-frequency LC network 1034 corresponding to and connected to the high-frequency oscillator 1010, the low-frequency LC network 1032 comprising electrical components that define a low natural electrical frequency response that matches a low natural physical frequency of the handpiece 114. This embodiment can further be wherein the high-frequency LC network 1034 further comprises different electrical components that define a high natural electrical frequency response that matches a high natural frequency of the handpiece 114. The high natural frequency being a physical resonance of the handpiece 114 (and optionally the needle 106) above 60 kHz.

Yet another embodiment of the present invention envisions a phacoemulsification configuration 1000 comprising a dual frequency voltage producing circuit 1002 comprising a low-frequency voltage pathway 1004 that includes a low-frequency oscillator 1008 and a low-frequency LC network 1032 and a high-frequency voltage pathway 1006 that includes a high-frequency oscillator 1010 and a high-frequency LC network 1034. A needle 106 extends from a handpiece 114 wherein the handpiece 114 includes piezoelectric crystals 116. The piezoelectric crystals 116 is electrically connected to the dual frequency voltage producing circuit 1002. When the high-frequency oscillator 1010 is in a high-frequency on state and the low-frequency oscillator 1008 is in a low-frequency off state, the needle 106 comprises a single node of minimum amplitude 870 (of FIG. 9) that has essentially no vibration displacement. When the low-frequency oscillator 1008 is in a low-frequency on state and the high-frequency oscillator 1010 is in an off state, the needle 106 does not comprise a single non-displacement region (shown in FIG. 8). FIGS. 8 and 9 are directed to a tapered horn 805, however these regions are not contingent on the tapered horn 805.

The phacoemulsification configuration 1000, further contemplating wherein the phacoemulsification configuration 1000 is only operably used (meaning during operation) for a cataract surgery.

The phacoemulsification configuration 1000, further imagining wherein the handpiece 114 comprises at least a low frequency mode 924 and a high frequency mode 922. The low-frequency LC network 1032 comprises a first set of electrical components, such as one or more capacitors, inductors, resistors, etc., that electrically match the low frequency mode 924 within +/−10% and the high-frequency LC network 1034 comprises a second set of electrical components that electrically match the high frequency mode 922 within +/−10%.

The phacoemulsification configuration 1000 further considering that the low-frequency pathway 1004 and the high-frequency pathway 1006 are located externally from the handpiece 114 and the needle 106. Certain embodiments envision the externally located circuit being in a power unit or box that connects to the handpiece 114 via wires or cables.

The phacoemulsification configuration 1000 further comprising a frequency mixer configured to produce a combined frequency output voltage, which is a combination of a low-frequency output voltage 924 from the low-frequency oscillator 1008 when in the low-frequency on state and a high-frequency output voltage 922 from the high-frequency oscillator 1010 when in the high-frequency on state. When the piezoelectric crystal transducer 116 is subjected to the combination frequency output voltage, the hollow phacoemulsification needle 106 comprises a single node of reduced amplitude 970 (of FIG. 11B), the single note of reduced amplitude 970 has higher displacement than the single node of minimum amplitude 870 (of FIG. 9). This embodiment contemplates that the frequency mixer (such as a tapped transformer or amplifier/s) is an operator controlled actuator that adjusts the high-frequency output voltage 922 inversely proportional to the low-frequency output voltage 924.

Still yet, another embodiment of the present invention contemplates a method for driving a phacoemulsification assembly 100. The phacoemulsification assembly 100 comprising a dual frequency producing circuit 1002 electrically connected to a phacoemulsification assembly 100 comprising a needle 106 extending from a handpiece 114. The handpiece 114 comprising piezoelectric crystals 116. The steps can include generating one of an independent high-frequency ringing in the needle 106, an independent low-frequency ringing in the needle 106 or a combination high-low frequency ringing in the needle 106. The high-frequency ringing of the needle 106 is produced by energizing the piezoelectric crystals 116 with a high-frequency voltage 922 from the dual frequency producing circuit 1002. The high-frequency ringing generates a high-frequency standing wave 819 comprising a single node of minimum amplitude 870 that is along the needle 106. The low-frequency ringing of the needle 106 is produced by energizing the piezoelectric crystals 116 with a low-frequency voltage 924 from the dual frequency producing circuit 1002. The low-frequency ringing of the needle 106 generates a low-frequency standing wave 817 that is devoid of any node of minimum amplitude 870 along the needle 106 (see FIG. 8 for example).

The method embodiment further comprising producing the combination high-low frequency ringing of the needle 106 by energizing the piezoelectric transducer 116/124 with both the low-frequency voltage 924 combined with the high-frequency voltage 922, a combined frequency standing wave 940 comprising a single node of low amplitude 970 along the needle 106 at the combination high-low frequency ringing, the node of low amplitude 970 is a higher amplitude then the node of minimum amplitude 870.

The method embodiment further contemplating the dual frequency circuit 1002 comprising a low-frequency voltage pathway 1004 that includes a low-frequency oscillator 1008 and a low-frequency LC network 1032 and a high-frequency voltage pathway 1006 comprising a high-frequency oscillator 1010 and a high-frequency LC network 1034. The low-frequency voltage pathway 1004 provides the low-frequency voltage 924 and the high-frequency voltage pathway 1006 provides the high-frequency voltage 922. The method embodiment further comprising balancing at least a portion of the low-frequency voltage pathway 1004 with electrical components that electrically oscillate within +/−10% of a low natural frequency of at least the handpiece 114.

Yet other embodiments contemplate a phacoemulsification device 800 for a phacoemulsification procedure, the phacoemulsification device 800 comprising: a handpiece 814 that includes a piezoelectric transducer 116/124 and a step horn 826; a needle 106 having a free distal tip 108 and a supported end structure 122 that is attached to the handpiece 814, the supported end structure 122 includes external threads that mate with internal threads in the handpiece 814, the needle 106 having a substantially cylindrical portion extending from the free distal tip 108 towards the step horn 826; a tapered section 805 in step horn 826, the step horn 826 is between the piezoelectric transducer 116/124 and the needle 106; and the piezoelectric transducer 116/124 configured to periodically vibrate the needle 106 at either a low mode (frequency) or a high mode (frequency), the substantially cylindrical portion devoid of a node of minimum amplitude at the low mode and the substantially cylindrical portion of needle 106 possessing a single node of minimum amplitude 870 at the high mode.

The surgical instrument embodiment further envisioning the low mode being below 60 kHz and the high mode is equal or above 60 kHz.

The surgical instrument embodiment further envisioning the tapered section is selected from a group consisting of a geometry that is conical, elliptical, Gaussian, exponential, and Fourier.

The surgical instrument embodiment further envisioning the piezoelectric transducer 116/124 being configured to switch between the high mode and the low mode by a surgeon command.

The surgical instrument embodiment further envisioning wherein the tapered section 805 extends approximately to the supported end structure 122.

The surgical instrument embodiment further envisioning the piezoelectric transducer 116/124 being is configured to switch automatically between the high mode and the low mode by a command received from the phaco machine controller 380.

The surgical instrument embodiment further envisioning a single node of minimum amplitude 835 along the tapered section 805 at the high mode and a single node of minimum amplitude 870 along the tapered substantially cylindrical section of the needle 106, which is shown by way of example in FIG. 9.

The surgical instrument embodiment further envisioning the free distal tip 108 being configured to periodically vibrate at a high amplitude in both the low mode and the high mode.

The surgical instrument embodiment further envisioning the tapered section being integral with the handpiece.

The surgical instrument embodiment further envisioning the piezoelectric transducer 116/124 being adapted to switch between the high mode and the low mode after a predetermined time interval.

Other embodiments contemplate a method to drive oscillations in a surgical instrument 800 during phacoemulsification, the method comprising: providing a handpiece 814 that includes a piezoelectric transducer 116/124 and a step horn 826, the step horn 826 possessing a tapered section 805 that tapers towards a distal handpiece end 828, a needle 106 having a free distal tip 108 and a supported end structure 122 that is attached to the distal handpiece end 828, the needle 106 possessing a length being defined along a longitudinal axis 902 of the needle 106; energizing the piezoelectric transducer 116/124 to periodically longitudinally expand and contract in at least two ultrasonic driving frequencies that rings the needle 106 with at least either a high ultrasonic standing wave 819 or a low ultrasonic standing wave 817; inserting the needle 106 in an eye 120; after the inserting step, energizing the piezoelectric transducer 116/124 to drive the needle 106 at either the high ultrasonic standing wave 819 or the low ultrasonic standing wave 817, only the high ultrasonic standing possessing a node of minimum amplitude 870 along the length 854 of the needle 106.

The method embodiment further envisioning the high and the low standing waves having a proximal node of minimum amplitude 835 along the tapered section 805.

The method embodiment further envisioning the high and the low standing waves having a distal anti-node of maximum amplitude 822/834 at the free distal tip 108.

The method further comprising switching the ultrasonic driving frequencies from ringing the needle 106 at the high ultrasonic standing wave 819 to the low ultrasonic standing wave 817 after a predetermined amount of time.

The method further comprising switching from the low ultrasonic standing wave 817 to the high ultrasonic standing wave 819 when the hollow titanium needle 106 becomes at least partially occluded and switching from the high ultrasonic standing wave 819 to the low ultrasonic standing wave 817 when the hollow titanium needle 106 is no longer partially occluded.

The method embodiment further envisioning the low ultrasonic standing wave 817 being defined by a frequency below 60 kHz and the high ultrasonic standing wave 819 is defined by a frequency equal to or above 60 kHz.

The method embodiment further envisioning the tapered section 805 being defined by a profile that is selected from a group consisting of a geometry that is conical, elliptical, Gaussian, exponential, and Fourier.

Yet another embodiment contemplates a phacoemulsification device comprising: a phacoemulsification device 800 possessing a handpiece 814 that tapers 805 to a tapered end 828, a needle 106 attached to the tapered end 828, the needle 106 having a substantially cylindrical portion that extends from approximately the tapered end 828 to a free distal tip 108; and a piezoelectric transducer 116/124 configured to drive the needle 106 with either a low ultrasonic standing wave 817 or a high ultrasonic standing wave 819, the high ultrasonic standing wave 819 having a single node of minimum amplitude 870 along the needle 106, the low ultrasonic standing wave 817 devoid of any node of minimum amplitude along the needle 106.

The phacoemulsification device embodiment further envisioning wherein the piezoelectric transducer 116/124 is configured to change between the low ultrasonic standing wave 817 and the high ultrasonic standing wave 819.

The phacoemulsification device embodiment further envisioning wherein the low ultrasonic standing wave 817 having a frequency of less than 60 kHz and the high ultrasonic standing wave 819 having a frequency of more than or equal to 60 kHz.

In a different embodiment, a phacoemulsification device 800 is contemplated comprising: a handpiece 814 that includes a piezoelectric transducer 116/124; a needle 106 having a free distal tip 108 and a supported end structure 122 that is attached to the handpiece 814, the supported end structure 122 includes external threads that mate with internal threads in the handpiece 814, the needle 106 having a substantially cylindrical portion extending from the free distal tip 108 towards the handpiece 814; and the piezoelectric transducer 116/124 configured to periodically vibrate the needle 106 with a standing wave 940 defined by a high frequency mode 922 superimposed over a low frequency mode 924, the standing wave 940 defining a single semi-node of low amplitude 970 along the substantially cylindrical portion of needle 106 and an anti-node of high amplitude 955 at the free distal tip 108.

The phacoemulsification device 800 embodiment further envisioning wherein the low frequency mode 924 is below 60 kHz and the high frequency mode 922 is equal or above 60 kHz.

The phacoemulsification device 800 embodiment further comprising a tapered section 805 between the piezoelectric transducer 116/124 and the substantially cylindrical portion of the needle 106.

The phacoemulsification device 800 embodiment further envisioning the piezoelectric transducer 116/124 being configured to be adjusted by a surgeon command to increase or decrease power of the high frequency mode 922 inversely to the low frequency mode 924.

The phacoemulsification device 800 embodiment further envisioning wherein the tapered section 805 extends approximately to the supported end structure 122.

The phacoemulsification device 800 embodiment further envisioning the piezoelectric transducer 116/124 configured to adjust power of the high frequency mode 922 inversely proportional to the low frequency mode 924 by a command received from the phaco machine controller 380.

The phacoemulsification device 800 embodiment further envisioning wherein there is a single node of low amplitude 935 located along the tapered section 805.

The phacoemulsification device 800 embodiment further envisioning wherein the low frequency mode 924 and the high frequency mode 922 both vibrate longitudinally along the needle 106.

The phacoemulsification device 800 embodiment further envisioning wherein the tapered section 805 is selected from a group consisting of a geometry that is conical, elliptical, Gaussian, exponential, and Fourier.

The phacoemulsification device 800 embodiment further envisioning wherein the piezoelectric transducer 116/124 is adapted to adjust power of the high frequency mode 922 inversely proportional to the low frequency mode 924.

Aspects of the present invention further contemplate a method to drive oscillations in a phacoemulsification device 800 during phacoemulsification, the phacoemulsification procedure method comprising: providing a handpiece 814 that includes a piezoelectric transducer arrangement 116/124, a needle 106 having a free distal tip 108 and a supported end structure 122 that is attached to the distal handpiece end 828, the needle 106 possessing a length being defined along a longitudinal axis 902 of the needle 106; energizing the piezoelectric transducer 116/124 to periodically longitudinally expand and contract in at least two simultaneously driving ultrasonic frequencies 920 made up of at least a high ultrasonic frequency 922 and a low ultrasonic frequency 924, the at least two simultaneously driving ultrasonic frequencies 920 ring the needle 106 with a standing wave 940 defined by at least a high ultrasonic standing wave 819 superimposed over a low ultrasonic standing wave 817; inserting the needle 106 in an eye 120; and after the inserting step, energizing the piezoelectric transducer 116/124 to drive the needle 106 at the simultaneously driving ultrasonic frequencies 920, the standing wave 940 defining a single semi-node of low amplitude 970 along the needle 106 and an anti-node of high amplitude 955 at the free distal tip 108.

The phacoemulsification procedure method embodiment further envisioning wherein the handpiece 814 further possesses a tapered section 805 that tapers towards a distal handpiece end 828.

The phacoemulsification procedure method embodiment further envisioning wherein the standing wave 940 has a proximal node of low amplitude 935 along the tapered section 805.

The phacoemulsification procedure method embodiment further envisioning wherein the anti-node of high amplitude 955 is a distal anti-node of maximum amplitude 955 at the free distal tip 108.

The phacoemulsification procedure method embodiment further comprising increasing power to the high frequency mode 922 while inversely decreasing the power to the low frequency mode 924, or decreasing the power to the high frequency mode 922 while inversely increasing the power to the low frequency mode 924.

The phacoemulsification procedure method embodiment further envisioning further comprising increasing the power to the high frequency mode 922 while inversely decreasing the power to the low frequency mode 924 when the needle 106 becomes at least partially occluded and switching from the high ultrasonic frequency mode 922 to the low ultrasonic frequency mode 924 when the needle 106 is no longer partially occluded.

The phacoemulsification procedure method embodiment further envisioning wherein the low ultrasonic frequency 924 is below 60 kHz and the high ultrasonic frequency 922 is equal to or above 60 kHz.

Other aspects of the present invention consider a hand-held surgical instrument comprising: a phacoemulsification device 800 possessing a handpiece 814, a needle 106 attached to the handpiece 814, the needle 106 having a substantially cylindrical portion that extends from approximately the handpiece 814 to a free distal tip 108; and a piezoelectric transducer 116/124 configured to drive the needle 106 with at least two simultaneous driving frequencies 922 and 924 that define a standing wave 940 with a single semi-node of low amplitude 970 along the hollow titanium needle 106 and an anti-node of high amplitude 955 at the free distal tip 108.

The hand-held surgical instrument embodiment further envisioning wherein the transducer 116/124 is configured to increase power to the high frequency mode 922 while inversely decreasing the power to the low frequency mode 924, or decrease the power to the high frequency mode 922 while inversely increasing the power to the low frequency mode 924.

The hand-held surgical instrument embodiment further envisioning wherein at least two simultaneous driving frequencies 920 comprise a high ultrasonic frequency 922 of equal to or more than 60 kHz and a low ultrasonic frequency 924 of less than 60 kHz.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe modulating between a high ultrasonic frequency and an ultrasonic (or low ultrasonic) frequency, it is contemplated that multiple ultrasonic frequencies and high ultrasonic frequencies can be used while still maintaining substantially the same functionality without departing from the scope and spirit of the present invention. Furthermore, though various LC circuit designs are described herein to provide structure, they are by example and by no way are limiting to the various potential circuit configurations that can be constructed to meet the functionality within the scope and spirit of the present invention. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A phacoemulsification arrangement for a phacoemulsification procedure, comprising:
    a needle extending from a handpiece that includes a piezoelectric transducer; and
    a dual frequency producing circuit comprising a low-frequency oscillator and a high-frequency oscillator,
        the dual frequency producing circuit is electrically connected to the piezoelectric transducer,
        the low-frequency oscillator is configured to drive the piezoelectric transducer that periodically vibrates the needle at a low frequency of less than 60 kHz, and
        the high-frequency oscillator is configured to drive the piezoelectric transducer that periodically vibrates the needle at a high frequency of greater than or equal to 60 kHz while producing a single node of minimum amplitude along the needle.

2. The phacoemulsification arrangement of claim 1, wherein the dual frequency producing circuit is external to the needle and the handpiece.

3. The phacoemulsification arrangement of claim 1, wherein the low-frequency oscillator is operable with the high-frequency oscillator to collectively periodically vibrate the needle with a hybrid standing wave that is defined by the low frequency standing wave superimposed over the high frequency standing wave.

4. The phacoemulsification arrangement of claim 3, further comprising an actuator configured to change a percent contribution of the low-frequency standing wave inversely proportional to the high-frequency standing wave when generating the hybrid standing wave.

5. The phacoemulsification arrangement of claim 3, wherein the hybrid standing wave causes a single node of reduced amplitude along the needle, wherein the single node of reduced amplitude is a higher amplitude than the single node of minimum amplitude.

6. The phacoemulsification arrangement of claim 1, wherein the dual frequency producing circuit comprises:
   a low-frequency pathway and a high-frequency pathway,
      the low-frequency pathway comprises a low-frequency LC network tied to the low-frequency oscillator, and the high-frequency pathway comprises a high-frequency LC network tied to the high-frequency oscillator; and
   a tapped output transformer inductively coupled to the low-frequency LC network and the high-frequency LC network,
      the tapped output transformer is electrically connected to the piezoelectric transducer, and
      the tapped output transformer is configured to drive the piezoelectric transducer with a low-frequency voltage from the low-frequency LC network, a high-frequency voltage from the high-frequency LC network, or combination of the high frequency voltage and the low-frequency voltage.

7. The phacoemulsification arrangement of claim 6, further comprising a low-frequency circuit resonance corresponding to the low-frequency LC network and a high-frequency circuit resonance corresponding to the high-frequency LC network,
   wherein the low frequency circuit resonance matching a first natural frequency of the needle and the handpiece, and
   wherein the high-frequency circuit resonance matching a second natural frequency of the and the handpiece.

8. The phacoemulsification arrangement of claim 1, wherein the needle and the handpiece are only applicable to cataract surgery using the phacoemulsification procedure.

9. The phacoemulsification arrangement of claim 1, wherein the dual frequency producing circuit further comprising a low-frequency LC network corresponding to and connected to the low-frequency oscillator and the high-frequency LC network corresponding to and connected to the high-frequency oscillator,
   wherein the low-frequency LC network comprising electrical components that define a low natural electrical frequency response that matches a low natural physical frequency of the handpiece.

10. The phacoemulsification arrangement of claim 9, wherein the high-frequency LC network further comprising different electrical components that define a high natural electrical frequency response that matches a high natural frequency of the handpiece.

11. A phacoemulsification configuration, comprising:
   a dual frequency voltage producing circuit comprising a low-frequency voltage pathway that includes a low-frequency oscillator and a low-frequency LC network and a high-frequency voltage pathway that includes a high-frequency oscillator and a high-frequency LC network;
   a needle extending from a handpiece, the handpiece including a piezoelectric transducer, the piezoelectric transducer electrically connected to the dual frequency voltage producing circuit;
      when the high-frequency oscillator is in a high-frequency on state and the low-frequency oscillator is in a low-frequency off state, the needle comprises a single non-displacement region that has essentially no vibration displacement, and when the low-frequency oscillator is in a low-frequency on state and the high-frequency oscillator is in an off state, the needle does not comprise a single non-displacement region.

12. The phacoemulsification configuration of claim 11, wherein the phacoemulsification configuration is only operably used for a cataract surgery.

13. The phacoemulsification configuration of claim 11, wherein the handpiece comprises at least a low natural frequency and a high natural frequency,
   wherein the low-frequency LC network comprises a first set of electrical components that electrically match the low natural frequency within +/−10%, and
   wherein the high-frequency LC network comprises a second set of electrical components that electrically match the high natural frequency within +/−10%.

14. The phacoemulsification configuration of claim 11, further comprising a frequency mixer configured to produce a combined frequency output voltage, which is a combination of a low-frequency output voltage from the low-frequency oscillator when in the low-frequency on state and a high-frequency output voltage from the high-frequency oscillator when in the high-frequency on state, wherein when the piezoelectric transducer is subjected to the combination frequency output voltage, the needle comprises a single low displacement region, the single low displacement region has higher displacement than the single non-displacement region.

15. The phacoemulsification configuration of claim 11, wherein the dual frequency voltage producing circuit is configured to shift in-phase a low-frequency voltage and low-frequency current produced by the low-frequency oscillator; and wherein the dual frequency voltage producing circuit is further configured to shift in-phase a high-frequency voltage and high-frequency current produced by the high-frequency oscillator.

16. The phacoemulsification configuration of claim 15, wherein the frequency mixer is an operator controlled actuator that adjusts the high-frequency output voltage inversely proportional to the low-frequency output voltage.

17. A method for driving a phacoemulsification assembly, comprising:
   providing a dual frequency producing circuit electrically connected to a phacoemulsification assembly comprising a needle extending from a handpiece, the handpiece comprising a piezoelectric transducer;
   generating one of an independent high-frequency ringing in the needle, an independent low-frequency ringing in the needle or a combination high-low frequency ringing in the needle;
   producing the high-frequency ringing by energizing the piezoelectric transducer with a high-frequency voltage from the dual frequency producing circuit, the high-frequency ringing causing a single node of minimum amplitude along the needle;
   producing the low-frequency ringing by energizing the piezoelectric transducer with a low-frequency voltage from the dual frequency producing circuit, the low-frequency ringing causing no node of minimum amplitude along the needle.

18. The method of claim 17, further comprising producing a combination of the low-frequency ringing and the high-frequency ringing by energizing the piezoelectric transducer with both the low-frequency voltage combined with the high-frequency voltage,
   the needle comprising a single node of low amplitude along the needle at the combination of the low-frequency ringing and the high-frequency ringing,
   wherein the node of low amplitude is a higher amplitude then the node of minimum amplitude.

19. The method of claim 17, wherein the dual frequency circuit comprises a low-frequency voltage pathway that includes a low-frequency oscillator and a low-frequency LC network and a high-frequency voltage pathway including a high-frequency oscillator and a high-frequency LC network, and wherein the low-frequency voltage pathway provides the low-frequency voltage and the high-frequency voltage pathway provides the high-frequency voltage.

20. The method of claim 19, further comprising balancing at least a portion of the low-frequency voltage pathway with electrical components that electrically oscillate within +/−10% of a low natural frequency of at least the handpiece.

* * * * *